(12) United States Patent
Nishio et al.

(10) Patent No.: US 7,234,341 B2
(45) Date of Patent: Jun. 26, 2007

(54) GAS SENSOR AND METHOD OF MANUFACTURING THE GAS SENSOR

(75) Inventors: Hisaharu Nishio, Nagoya (JP); Takashi Nakao, Nagoya (JP); Kazuhiro Kouzaki, Nagoya (JP)

(73) Assignee: NGK Spark Plug Co., Ltd., Aichi-ken (JP)

( * ) Notice: Subject to any disclaimer, the term of this patent is extended or adjusted under 35 U.S.C. 154(b) by 0 days.

(21) Appl. No.: 10/564,354

(22) PCT Filed: Jul. 13, 2004

(86) PCT No.: PCT/JP2004/009971

§ 371 (c)(1),
(2), (4) Date: Jan. 12, 2006

(87) PCT Pub. No.: WO2005/008233

PCT Pub. Date: Jan. 27, 2005

(65) Prior Publication Data

US 2006/0174690 A1    Aug. 10, 2006

(30) Foreign Application Priority Data

Jul. 17, 2003    (JP) .............................. 2003-198557

(51) Int. Cl.
    *G01N 7/00*    (2006.01)
(52) U.S. Cl. .................................................... 73/23.31
(58) Field of Classification Search ............... 73/23.31, 73/23.32, 31.05, 31.06; 204/424, 425, 426, 204/427, 428, 429
    See application file for complete search history.

(56) References Cited

U.S. PATENT DOCUMENTS

| | | | | |
|---|---|---|---|---|
| 4,206,173 A | * | 6/1980 | Yamaguchi et al. | .......... 422/98 |
| 4,210,510 A | * | 7/1980 | Grimes | ........................ 204/428 |
| 4,401,967 A | * | 8/1983 | Miwa et al. | ................... 338/34 |
| 4,403,207 A | * | 9/1983 | Murphy et al. | ................ 338/34 |
| 4,569,748 A | * | 2/1986 | Yamakawa et al. | .......... 204/429 |
| 4,668,477 A | * | 5/1987 | Nishio et al. | ................... 422/98 |
| 6,276,191 B1 | * | 8/2001 | Schneider et al. | .......... 73/23.31 |
| 6,513,363 B2 | * | 2/2003 | Asai et al. | ................... 73/31.05 |

FOREIGN PATENT DOCUMENTS

| | | |
|---|---|---|
| JP | 53-95884 A | 12/1951 |
| JP | 53-67494 A | 6/1978 |

(Continued)

*Primary Examiner*—Michael Cygan
(74) *Attorney, Agent, or Firm*—Sughrue Mion, PLLC

(57) ABSTRACT

An object is to provide a gas sensor which can suppress positional shift of a to-be-held member such as a gas detection element, as well as a method of manufacturing the gas sensor. A gas sensor (101) includes a gas detection element (111), a metallic shell (131), a plate packing (157), and a first packing (159). A proximal end surface (113*t*2) of a projection (113) of the gas sensor element (111) and a central inner circumferential surface (135*n*) of the metallic shell (131) form an acute-angle clearance (120). The first packing (159), which has a wedge-like cross section, is disposed in the clearance (120) such that the first packing (159) is pressed against the proximal end surface (113*t*2) of the projection (113) of the gas sensor element (111) and the central inner circumferential surface (135*n*) of the metallic shell (131).

17 Claims, 13 Drawing Sheets

FOREIGN PATENT DOCUMENTS

| | | |
|---|---|---|
| JP | 53-98895 A | 8/1978 |
| JP | 53-105285 A | 9/1978 |
| JP | 54-58194 B | 4/1979 |
| JP | 60-150450 U | 10/1985 |
| JP | 2002-286684 A | 10/2002 |

* cited by examiner

GAS SENSOR AND METHOD OF MANUFACTURING THE GAS SENSOR

TECHNICAL FIELD

The present invention relates to a gas sensor for detecting a certain gas contained in a gas to be measured, as well as to a method of manufacturing the gas sensor. More particularly, the invention relates to a gas sensor configured such that a to-be-held member, such as a closed-bottomed tubular gas detection element or an element holder, is held in a tubular metallic shell, as well as to a method of manufacturing the gas sensor.

BACKGROUND ART

A conventionally known gas sensor is configured such that a closed-bottomed tubular gas detection element (to-be-held member) is held in a tubular metallic shell. An example of such a gas sensor is shown in FIG. 13, which shows a partial cross section of a gas sensor. A gas sensor 901 shown in FIG. 13 is an oxygen sensor attached to an exhaust gas pipe of an internal combustion engine and adapted to measure oxygen concentration in exhaust gas. The gas sensor 901 includes a closed-bottomed tubular gas detection element 911, whose distal end (a lower end in FIG. 13) along the direction of an axis C is closed, and a tubular metallic shell 931, which coaxially holds the gas detection element 911 therein.

The gas detection element 911 includes a projection 913, which is circumferentially formed at the central portion of the gas detection element 911 with respect to the direction of the axis C and projects radially outward. The projection 913 has a first tapered outer circumferential surface 913$t$1 (also referred to as a "distal end surface") which is located on its distal end and whose diameter increases from its distal end side toward its proximal end side, a second tapered outer circumferential surface 913$t$2 (also referred to as a "proximal end surface") which is located on its proximal end and whose diameter increases from its proximal end side toward its distal end side, and a central outer cylindrical surface 913$m$ extending therebetween. The gas detection element 911 is formed from an oxygen-ion-conductive solid electrolyte. The gas detection element 911 has an inner electrode 915 cladding an inner circumferential surface 911$n$, and an outer electrode 917 cladding an outer circumferential surface 911$m$.

The metallic shell 931 includes a distal end section 933 (a lower section in FIG. 13), a central section 935, and a proximal section 937 (an upper section in FIG. 13). A through-hole whose wall is an inner circumferential surface 931$n$ extends through the metallic shell 931, and its diameter reduces from the side toward the proximal end to the side toward the distal end.

The distal end section 933 has an inner circumferential surface 933$n$ having a relatively small diameter, and a male-threaded portion 933$g$ formed on its outer circumference and adapted to attach the gas sensor 901 to the exhaust gas pipe. A protection cap 951 is attached to a distal end portion of the distal end section 933 for the purpose of protecting a distal end section of the gas detection element 911. The protection cap 951 assumes a closed-bottomed tubular shape and has a number of gas introduction holes 951$k$ for introducing exhaust gas into the interior of the gas sensor 901 from the exhaust pipe. A gasket 953 is attached to a proximal end portion of the distal end section 933.

The central section 935 is composed of a stepped portion 935$b$ having a tapered inner circumferential surface 935$t$1 (also referred to as a "support surface"), which is connected with the inner circumferential surface 933$n$ of the distal end section 933 and whose diameter increases toward the proximal end side of the gas sensor; a tubular portion 935$c$ having a central inner circumferential surface 935$n$, which is connected with the tapered inner circumferential surface 935$t$1 and which has a diameter larger than that of the inner circumferential surface 933$n$. A radially outer portion of the central section 935 is formed into a hexagonal flange portion (a tool engagement portion) 935$r$, which is used in attaching the gas sensor 901 to the exhaust gas pipe.

The proximal end section 937 has an inner circumferential surface 937$n$, which is connected with the central inner circumferential surface 935$n$ of the central section 935 and which has a diameter greater than that of the central inner circumferential surface 935$n$.

An annular plate packing 957 of metal is disposed on the tapered inner circumferential surface 935$t$1 of the central section 935 of the metallic shell 931. The first tapered outer circumferential surface 913$t$1 of the projection 913 of the gas detection element 911, which is coaxially inserted into the metallic shell 931, abuts the plate packing 957. In other words, the stepped portion 935$b$ of the central section 935 of the metallic shell 931 and the projection 913 of the gas detection element 911 are engaged via the plate packing 957. Since the outer electrode 917 is also formed on the projection 913, the metallic shell 931 and the outer electrode 917 of the gas detection element 911 are electrically connected via the plate packing 957.

A C-type first wire packing 959 is disposed in such a manner as to abut the second tapered outer circumferential surface 913$t$2 of the projection 913 of the inserted gas detection element 911 and the inner circumferential surface 931$n$ (the inner circumferential surface 937$n$ of the proximal end section 937) of the metallic shell 931.

In a region located toward the proximal end of the gas sensor with respect to the first wire packing 959, a powder is charged into an annular clearance provided between the outer circumferential surface 911$m$ of a proximal end portion of the gas detection element 911 and the inner circumferential surface 931$n$ (the inner circumferential surface 937$n$ of the proximal end section 937) of the metallic shell 931, thereby forming a charged seal layer 961.

In a region located toward the proximal end of the gas sensor with respect to the charged seal layer 961, a distal end section 973 of a sleeve 971 is inserted into an annular clearance provided between the outer circumferential surface 911$m$ of the gas detection element 911 and the inner circumferential surface 931$n$ (the inner circumferential surface 937$n$ of the proximal end section 937) of the metallic shell 931. The distal end section 973 of the sleeve 971 assumes the form of a circumferential projection projecting radially outward and has a tapered outer circumferential surface 973$m$ whose diameter increases toward the distal end side of the gas sensor. A C-type second wire packing 965 is disposed on the tapered outer circumferential surface 973$m$. The distal end of the distal end section 937 of the metallic shell 931 is bent radially inward in such a manner as to cover the second wire packing 965, thereby compressing the second wire packing 965 by means of crimping. The compressive crimping action also axially compresses the first wire packing 959 and the charged seal layer 961. As a result, the first wire packing 959 is elastically deformed. An elastic force induced by the elastic deformation coaxially holds the gas detection element 911 in the metallic shell 931.

An element-side terminal 981 is inserted into the gas detection element 911 and electrically connected with the inner electrode 915 of the gas detection element 911.

A Document related to the above technique is disclosed in, for example, Patent Document 1.

Patent Document 1: Japanese Utility Model Application Laid-Open (kokai) No. 53-95884

DISCLOSURE OF THE INVENTION

Problems to be Solved by the Invention

However, in the conventional gas sensor 901, the first wire packing 959 is only caused to be pressed and elastically deformed by means of crimping on the metallic shell 931. When, as a result of long-term use of the gas sensor 901, loosening of the crimp or a like phenomenon occurs with a resultant drop in compressive stress exerted on the charged seal layer 961, the first wire packing 959 becomes loose, and thus the gas detection element 911 shifts, which may adversely affect, for example, the accuracy of detection of exhaust gas.

In addition, when the first wire packing 959 becomes loose, particles of a powder used to form the charged seal layer 961 leak toward the distal-end side through the clearance between the outer circumferential surface 911m of the gas detection element 911 and the inner circumferential surface 931n of the metallic shell 931.

Moreover, in the conventional gas sensor 901, the metallic shell 931 and the outer electrode 917 of the gas detection element 911 are electrically connected via the plate packing 957. Therefore, when loosening of the crimp or a like phenomenon occurs with a resultant drop in compressive stress exerted on the charged seal layer 961, whereby the first wire packing 959 becomes loose and the gas detection element 911 shifts, the contact between the plate packing 957 and the gas detection element 911 (the outer electrode 917 on the first tapered outer circumferential surface 913t) and that between the plate packing 957 and the metallic shell 931 (the tapered inner circumferential surface 935t1) become incomplete. As a result, the reliability of electrical connection between the outer electrode 917 and the metallic shell 931 is impaired. When the first wire packing 959 becomes loose, the following problem may also arise. Particles of a powder used to form the charged seal layer 961 pass through a clearance between the outer circumferential surface 911m of the gas detection element 911 and the inner circumferential surface 931n of the metallic shell 931 and reach a region where the plate packing 957 is provided. The particles enter between the plate packing 957 and the gas detection element 911 or between the plate packing 957 and the metallic shell 931, causing defective electrical contact between the plate packing 957 and the gas detection element 911 or between the plate packing 957 and the metallic shell 931.

According to the method of manufacturing the conventional gas sensor 901, after the plate packing 957 and the gas detection element 911 are inserted into the metallic shell 931, the first wire packing 959 is inserted, and then a powder is charged. Subsequently, the sleeve 971 and the second wire packing 965 are inserted. The proximal end of the metallic shell 931 is crimped, thereby providing the gas detection element 911 in the metallic shell 931 in a fixed condition.

However, the above method may involve the following problem. During the time between charging of a powder and crimping of the metallic shell 931, particles of the powder, which are expected to be all checked by the first wire packing 959, pass through a clearance between the outer circumferential surface 911m of the gas detection element 911 and the inner circumferential surface 931n of the metallic shell 931 and reach a region where the plate packing 959 is provided. The particles enter between the plate packing 959 and the gas detection element 911 or between the plate packing 959 and the metallic shell 931, causing defective electrical contact between the plate packing 957 and the gas detection element 911 or between the plate packing 957 and the metallic shell 931.

In view of the foregoing, an object of the present invention is to provide a gas sensor which can suppress more reliably the positional shift of a to-be-held member, such as a gas detection element or an element holder, as well as a method of manufacturing the gas sensor.

Means for Solving the Problems

Means for solution is a gas sensor comprising a to-be-held member having a distal-end-side holding surface and a proximal-end-side holding surface located on the proximal end side with respect to the distal-end-side holding surface; a tubular metallic shell having a stepped portion projecting radially inward from its inner circumferential surface, and adapted to hold the to-be-held member therein while surrounding the to-be-held member from radially outside and supporting the distal-end-side holding surface of the to-be-held member by a support surface of the stepped portion; and a first packing abutting the proximal-end-side holding surface of the to-be-held member and the inner circumferential surface of the metallic shell, wherein the first packing is disposed in an acute-angle clearance formed between the proximal-end-side holding surface of the to-be-held member and the inner circumferential surface of the metallic shell such that the first packing has a wedge-like cross section and is pressed against the proximal-end-side holding surface of the to-be-held member and the inner circumferential surface of the metallic shell.

In the conventional gas sensor, the wire packing is elastically deformed in the axial direction to thereby partially abut the proximal-end-side holding surface of the to-be-held member and the inner circumferential surface of the metallic shell. By contrast, in the gas sensor of the present invention, the first packing, which corresponds to the conventional wire packing, is disposed in an acute-angle clearance formed between the proximal-end-side holding surface of the to-be-held member and the inner circumferential surface of the metallic shell such that the first packing has a wedge-like cross section and is pressed against the proximal-end-side holding surface of the to-be-held member and the inner circumferential surface of the metallic shell. Thus, even when no external stress is exerted on the first packing, the first packing can fix the to-be-held member in the metallic shell. Therefore, even when, as a result of long-term use of the gas sensor, loosening of the crimp or a like phenomenon occurs, the first packing is less likely to become loose as compared with a conventional counterpart. Accordingly, positional shift of the to-be-held member can be suppressed more reliably.

No particular limitation is imposed on the type of a gas sensor, so long as the above requirements are met. Examples of such a gas sensor include an oxygen sensor, an $NO_x$ sensor, an HC sensor, and a $CO_2$ sensor.

Further, the expression "the metallic shell holds the to-be-held member therein" encompasses holding the entirety of the to-be-held member within the metallic shell and holding a portion of the to-be-held member within the metallic shell.

The first packing is not necessarily required to have a wedge-like cross section over the entire circumference of the packing disposed in the above-described clearance. The first packing is only required to have a wedge-like cross section at least over a portion of the circumference thereof. The first packing is not necessarily required to have a wedge-like shape over the entire cross section. The first packing is only required to have a wedge-like cross section at least in a distal-end-side portion thereof.

In the above-described gas sensor, preferably, the to-be-held member is a gas detection element having a projection which includes the distal-end-side holding surface and the proximal-end-side holding surface and which projects radially outward, the gas detection element assuming a closed-bottomed tubular shape with an axially distal end closed.

According to this invention, the to-be-held member is a gas detection element having a closed-bottomed tubular shape. Since this gas detection element has a projection which includes the distal-end-side holding surface and the proximal-end-side holding surface and which projects radially outward, the first packing is pressed against the proximal-end-side holding surface of the projection of the gas detection element, and is also pressed against the inner circumferential surface of the metallic shell. In such a gas sensor, even when no external stress is exerted on the first packing, the first packing can fix the gas detection element in the metallic shell. Therefore, even when, as a result of long-term use of the gas sensor, loosening of the crimp or a like phenomenon occurs, the first packing is less likely to become loose as compared with a conventional counterpart. Accordingly, positional shift of the gas detection element can be suppressed more reliably.

Preferably, the above-described gas sensor further comprises a gas detection element extending along the axial direction, wherein the to-be-held member is an element holder which has the distal-end-side holding surface, the proximal-end-side holding surface, and an opening through which the gas detection element is passed.

According to this invention, the to-be-held member is an element holder, through which a gas detection element is passed. Since this element holder has the distal-end-side holding surface and the proximal-end-side holding surface, the first packing is pressed against the proximal-end-side holding surface of the element holder, and is also pressed against the inner circumferential surface of the metallic shell. In such a gas sensor, even when no external stress is exerted on the first packing, the first packing can fix the element holder in the metallic shell. Therefore, even when, as a result of long-term use of the gas sensor, loosening of the crimp or a like phenomenon occurs, the first packing is less likely to become loose as compared with a conventional counterpart. Accordingly, positional shift of the element holder can be suppressed more reliably.

The above-described gas sensor further comprises a charged seal layer, which is formed by means of charging a powder into a clearance between the outer circumferential surface of the gas detection element and the inner circumferential surface of the metallic shell in a region located toward the proximal end of the gas sensor with respect to the first packing.

According to the present invention, the charged seal layer formed of a powder is provided in a clearance between the outer circumferential surface of the gas detection element and the inner circumferential surface of the metallic shell, thereby enhancing the performance of sealing the clearance between the gas detection element and the metallic shell.

The conventional gas sensor potentially involves the following problem. As a result of long-term use of the gas sensor, loosening of the crimp or a like phenomenon occurs. As a result, particles of a powder leak toward the distal end side through the clearance between the outer circumferential surface of the projection of the gas detection element and the inner circumferential surface of the metallic shell, or the clearance between the outer circumferential surface of the element holder and the inner circumferential surface of the metallic shell.

However, in the present invention, the first packing is disposed in an acute-angle clearance formed between the proximal-end-side holding surface of the to-be-held member (the gas detection element or the element holder) and the inner circumferential surface of the metallic shell such that the first packing has a wedge-like cross section and is pressed against the proximal-end-side holding surface of the to-be-held member and the inner circumferential surface of the metallic shell. Thus, even when, as a result of long-term use of the gas sensor, loosening of the crimp or a like phenomenon occurs, particles of a powder can be prevented from leaking toward the distal end side through the clearance between the outer circumferential surface of the projection of the gas detection element and the inner circumferential surface of the metallic shell, or the clearance between the outer circumferential surface of the element holder and the inner circumferential surface of the metallic shell.

In the above-described gas sensor, preferably, the first packing is formed by axially pressing and plastically deforming a wire packing, which has been inserted into the clearance between the proximal-end-side holding surface of the to-be-held member and the inner circumferential surface of the metallic shell, such that the first packing has a wedge-like cross section.

According to the present invention, the first packing is formed by axially pressing and plastically deforming a wire packing, which has been inserted into the clearance between the proximal-end-side holding surface of the to-be-held member and the inner circumferential surface of the metallic shell, such that the first packing has a wedge-like cross section. Since such a first packing has a wedge-like cross section as a result of being strongly pressed and plastically deformed, the first wire packing is strongly pressed against the proximal-end-side holding surface of the to-be-held member and the inner circumferential surface of the metallic shell. Accordingly, the to-be-held member and the metallic shell can be strongly fixed together.

In the above-descried gas sensor, preferably, the proximal-end-side holding surface of the to-be-held member and the inner circumferential surface of the metallic shell assume respective shapes such that in at least a distal-end-side portion of the clearance, the angle formed by the proximal-end-side holding surface and the inner circumferential surface decreases toward the distal end side, and the first packing is disposed to extend to the portion of the clearance where the angle formed by the proximal-end-side holding surface and the inner circumferential surface decreases toward the distal end side.

According to the present invention, the proximal-end-side holding surface of the to-be-held member and the inner circumferential surface of the metallic shell assume respective shapes such that in at least a distal-end-side portion of the clearance, the angle formed by the proximal-end-side holding surface and the inner circumferential surface decreases toward the distal end side. Further, the first packing is disposed to extend to such a portion. Therefore, the wedge effect increases toward the distal end side of the first packing, so that the to-be-held member and the metallic shell can be fixed together more firmly.

Another means for solution is a gas sensor comprising a gas detection element assuming a closed-bottomed tubular shape with an axially distal end closed, having an outer electrode formed on its outer circumferential surface, and having a projection projecting radially outward; a tubular metallic shell having a stepped portion projecting radially inward from its inner circumferential surface, and adapted to hold the gas detection element therein while surrounding the gas detection element from radially outside and supporting a distal end surface of the projection by a support surface of the stepped portion, the support surface of the stepped portion abutting the outer electrode formed on the distal end surface of the projection to thereby be electrically connected with the outer electrode; and a first packing abutting a proximal end surface of the projection and the inner circumferential surface of the metallic shell, wherein the first packing is disposed in an acute-angle clearance formed between the proximal end surface of the projection and the inner circumferential surface of the metallic shell such that the first packing has a wedge-like cross section and is pressed against the proximal end surface of the projection and the inner circumferential surface of the metallic shell.

In the conventional gas sensor, the wire packing is elastically deformed in the axial direction to thereby partially abut the proximal end surface of the projection of the gas detection element and the inner circumferential surface of the metallic shell. By contrast, in the gas sensor of the present invention, the first packing, which corresponds to the conventional wire packing, disposed in the acute-angle clearance formed between the proximal end surface of the projection and the inner circumferential surface of the metallic shell such that the first packing has a wedge-like cross section and is pressed against the proximal end surface of the projection and the inner circumferential surface of the metallic shell. Thus, even when no external stress is exerted on the first packing, the first packing can fix the gas detection element in the metallic shell. Therefore, even when, as a result of long-term use of the gas sensor, loosening of the crimp or a like phenomenon occurs, the first packing is less likely to become loose as compared with a conventional counterpart, thereby suppressing positional shift of the gas detection element and occurrence of defective contact between the support surface of the stepped portion of the metallic shell and the outer electrode formed on the distal end surface of the projection of the gas detection element. Thus, the reliability of electrical connection between the metallic shell and the outer electrode of the gas detection element can be enhanced.

Another means for solution is a gas sensor comprising a gas detection element assuming a closed-bottomed tubular shape with an axially distal end closed, having an outer electrode formed on its outer circumferential surface, and having a projection projecting radially outward; a tubular metallic shell having a stepped portion projecting radially inward from its inner circumferential surface, and adapted to hold the gas detection element therein while surrounding the gas detection element from radially outside and supporting a distal end surface of the projection by a support surface of the stepped portion; a first packing abutting a proximal end surface of the projection and the inner circumferential surface of the metallic shell; and a second packing of metal disposed between the distal end surface of the projection and the support surface of the stepped portion, and abutting the support surface of the stepped portion and the outer electrode formed on the distal end surface of the projection to thereby electrically connect the metallic shell and the outer electrode, wherein the first packing is disposed in an acute-angle clearance formed between the proximal end surface of the projection and the inner circumferential surface of the metallic shell such that the first packing has a wedge-like cross section and is pressed against the proximal end surface of the projection and the inner circumferential surface of the metallic shell.

In the gas sensor of the present invention, the first packing is disposed in the acute-angle clearance formed between the proximal end surface of the projection of the gas detection element and the inner circumferential surface of the metallic shell such that the first packing has a wedge-like cross section and is pressed against the proximal end surface of the projection and the inner circumferential surface of the metallic shell. Thus, even when no external stress is exerted on the first packing, the first packing can fix the gas detection element in the metallic shell. Therefore, even when, as a result of long-term use of the gas sensor, loosening of the crimp or a like phenomenon occurs, the first packing is less likely to become loose as compared with a conventional counterpart, thereby suppressing positional shift of the gas detection element and occurrence of defective contact between the second packing and the outer electrode formed on the distal end surface of the projection of the gas detection element and between the second packing and the support surface of the stepped portion of the metallic shell. Thus, the reliability of electrical connection between the metallic shell and the outer electrode of the gas detection element can be enhanced.

The above gas sensor further comprises a charged seal layer, which is formed by means of charging a powder into a clearance between the outer circumferential surface of the gas detection element and the inner circumferential surface of the metallic shell in a region located toward the proximal end of the gas sensor with respect to the projection of the gas detection element.

According to the present invention, the charged seal layer formed of a powder is provided in a clearance between the outer circumferential surface of the gas detection element and the inner circumferential surface of the metallic shell, thereby enhancing the performance of sealing the clearance between the gas detection element and the metallic shell.

The conventional gas sensor potentially involves the following problem. As a result of long-term use of the gas sensor, loosening of the crimp or a like phenomenon occurs. As a result, particles of a powder pass through a clearance between the outer circumferential surface of the projection of the gas detection element and the inner circumferential surface of the metallic shell and reach a region where the plate packing is provided. The particles enter between the plate packing and the gas detection element or between the plate packing and the metallic shell, causing defective contact therebetween and thus resulting in defective electrical contact therebetween.

However, in the present invention, the first packing is disposed in the acute-angle clearance formed between the proximal end surface of the projection of the gas detection element and the inner circumferential surface of the metallic shell such that the first packing has a wedge-like cross section and is pressed against the proximal end surface of the projection and the inner circumferential surface of the metallic shell. Thus, even when, as a result of long-term use of the gas sensor, loosening of the crimp or a like phenomenon occurs, such a structural feature of the first packing suppresses occurrence of the following problem: particles of a powder pass through a clearance between the outer circumferential surface of the projection of the gas detection element and the inner circumferential surface of the metallic shell and reach a region where the second packing is provided; and the particles enter between the second packing and the gas detection element or between the second packing and the metallic shell, causing defective contact therebetween.

In either of the above gas sensors provided by the present invention, the first packing is made of metal and abuts the outer electrode formed on the proximal end surface of the projection and the inner circumferential surface of the metallic shell to thereby electrically connect the outer electrode and the metallic shell.

According to the present invention, the first packing abuts the outer electrode formed on the proximal end surface of the projection of the gas detection element and the inner circumferential surface of the metallic shell to thereby electrically connect the metallic shell and the outer electrode of the gas detection element. Thus, the metallic shell and the outer electrode of the gas detection element can be electrically connected in a more reliable condition.

In the above-described gas sensor, preferably, the first packing is formed by axially pressing and plastically deforming a wire packing, which has been inserted into the clearance between the proximal end surface of the projection and the inner circumferential surface of the metallic shell, such that the first packing has a wedge-like cross section.

According to the present invention, the first packing is formed by axially pressing and plastically deforming a wire packing, which has been inserted into the clearance between the proximal end surface of the projection and the inner circumferential surface of the metallic shell, such that the first packing has a wedge-like cross section. Since such a first packing has a wedge-like cross section as a result of being strongly pressed and plastically deformed, the first wire packing is strongly pressed against the proximal end surface of the projection and the inner circumferential surface of the metallic shell. Accordingly, the gas detection element and the metallic shell can be strongly fixed together.

In the above-descried gas sensor, preferably, the proximal end surface of the projection and the inner circumferential surface of the metallic shell assume respective shapes such that in at least a distal-end-side portion of the clearance, the angle formed by the proximal end surface and the inner circumferential surface decreases toward the distal end side, and the first packing is disposed to extend to the portion of the clearance where the angle formed by the proximal end surface and the inner circumferential surface decreases toward the distal end side.

According to the present invention, the proximal end surface of the projection and the inner circumferential surface of the metallic shell assume respective shapes such that in at least a distal-end-side portion of the clearance, the angle formed by the proximal end surface and the inner circumferential surface decreases toward the distal end side. Further, the first packing is disposed to extend to such a portion. Therefore, the wedge effect increases toward the distal end side of the first packing, so that the gas detection element and the metallic shell can be fixed together more firmly.

Another solution is a method of manufacturing a gas sensor comprising a gas detection element assuming a closed-bottomed tubular shape with an axially distal end closed, having an outer electrode formed on its outer circumferential surface, and having a projection projecting radially outward; a tubular metallic shell having a stepped portion projecting radially inward from its inner circumferential surface, and adapted to hold the gas detection element therein while surrounding the gas detection element from radially outside and supporting a distal end surface of the projection by a support surface of the stepped portion, the support surface of the stepped portion abutting the outer electrode formed on the distal end surface of the projection to thereby be electrically connected with the outer electrode; and a first packing abutting a proximal end surface of the projection and the inner circumferential surface of the metallic shell. The method comprises an element-inserting step of inserting the gas detection element into the metallic shell; a wire-packing-inserting step of inserting a wire packing, which is to become the first packing, into the metallic shell; and a first-packing-forming step of axially pressing the wire packing inserted into the metallic shell such that the wire packing is plastically deformed so as to form the first packing which is disposed in an acute-angle clearance formed between the proximal end surface of the projection and the inner circumferential surface of the metallic shell such that the first packing has a wedge-like cross section and is pressed against the proximal end surface of the projection and the inner circumferential surface of the metallic shell.

According to the present invention, after the gas detection element is inserted into the metallic shell (the element-inserting step), the wire packing is inserted (the wire-packing-inserting step). Then, the wire packing is axially pressed such that the wire packing is plastically deformed so as to form the first packing which is disposed in the acute-angle clearance formed between the proximal end surface of the projection and the inner circumferential surface of the metallic shell such that the first packing has a wedge-like cross section and is pressed against the proximal end surface of the projection and the inner circumferential surface of the metallic shell (the first-packing-forming step). The first packing formed through elastic deformation is strongly pressed against the proximal end surface of the projection of the gas detection element, and is strongly pressed against the inner circumferential surface of the metallic shell. Thus, even when no external stress is exerted on the first packing, the first packing can fix the gas detection element in the metallic shell. Therefore, even when, as a result of long-term use of the gas sensor, loosening of the crimp or a like phenomenon occurs, the first packing is less likely to become loose as compared with a conventional counterpart, thereby suppressing positional shift of the gas detection element and occurrence of defective contact between the support surface of the stepped portion of the metallic shell and the outer electrode formed on the distal end surface of the projection of the gas detection element. Thus, the reliability of electrical connection between the metallic shell and the outer electrode of the gas detection element can be enhanced. Additionally, since the first packing is formed by means of plastically deforming the wire packing, the gas sensor can be readily manufactured at low cost.

Another solution is a method of manufacturing a gas sensor comprising a gas detection element assuming a closed-bottomed tubular shape with an axially distal end closed, having an outer electrode formed on its outer circumferential surface, and having a projection projecting radially outward; a tubular metallic shell having a stepped portion projecting radially inward from its inner circumferential surface, and adapted to hold the gas detection element therein while surrounding the gas detection element from radially outside and supporting a distal end surface of the projection by a support surface of the stepped portion; a first packing abutting a proximal end surface of the projection and the inner circumferential surface of the metallic shell; and a second packing of metal disposed between the distal end surface of the projection and the support surface of the stepped portion, and abutting the outer electrode formed on the distal end surface of the projection and the support surface of the stepped portion to thereby electrically connect the outer electrode and the metallic shell. The method comprises a second-packing-inserting step of inserting the second packing into the metallic shell; an element-inserting step of, after the second-packing-inserting step, inserting the gas detection element into the metallic shell; a second-packing-pressing step of, after the element-inserting step, axially pressing the gas detection element and the second packing inserted into the metallic shell to thereby bring the second packing into close contact with the support surface of the stepped portion; a wire-packing-inserting step of, after the second-packing-pressing step, inserting a wire packing, which is to become the first packing, into the metallic shell; and a first-packing-forming step of axially pressing the wire packing inserted into the metallic shell such that the wire packing is plastically deformed so as to form the first packing which is disposed in an acute-angle clearance formed between the proximal end surface of the projection and the inner circumferential surface of the metallic shell such that the first packing has a wedge-like cross section and is pressed against the proximal end surface of the projection and the inner circumferential surface of the metallic shell.

According to the present invention, after the second packing is inserted into the metallic shell (the second-packing-inserting step), the gas detection element is inserted (the element-inserting step). Then, the gas detection element and the second packing are axially pressed, to thereby bring the second packing in close contact with the support surface of the stepped portion of the metallic shell (the second-packing-pressing step). Thus, the contact between the second packing and the metallic shell is enhanced.

Subsequently, the wire packing is inserted (the wire-packing-inserting step). Then, the wire packing is axially pressed such that the wire packing is plastically deformed so as to form the first packing which is disposed in the acute-angle clearance formed between the proximal end surface of the projection and the inner circumferential surface of the metallic shell such that the first packing has a wedge-like cross section and is pressed against the proximal end surface of the projection and the inner circumferential surface of the metallic shell (the first-packing-forming step). The first packing formed through elastic deformation is strongly pressed against the proximal end surface of the projection of the gas detection element, and is strongly pressed against the inner circumferential surface of the metallic shell. Thus, even when no external stress is exerted on the first packing, the first packing can fix the gas detection element in the metallic shell. Therefore, even when, as a result of long-term use of the gas sensor, loosening of the crimp or a like phenomenon occurs, the first packing is less likely to become loose as compared with a conventional counterpart, thereby suppressing positional shift of the gas detection element and occurrence of defective contact between the support surface of the stepped portion of the metallic shell and the outer electrode formed on the distal end surface of the projection of the gas detection element. Thus, the reliability of electrical connection between the metallic shell and the outer electrode of the gas detection element can be enhanced. Additionally, since the first packing is formed by means of plastically deforming the wire packing, the gas sensor can be readily manufactured at low cost.

DESCRIPTION OF REFERENCE NUMERALS

Figure 1:
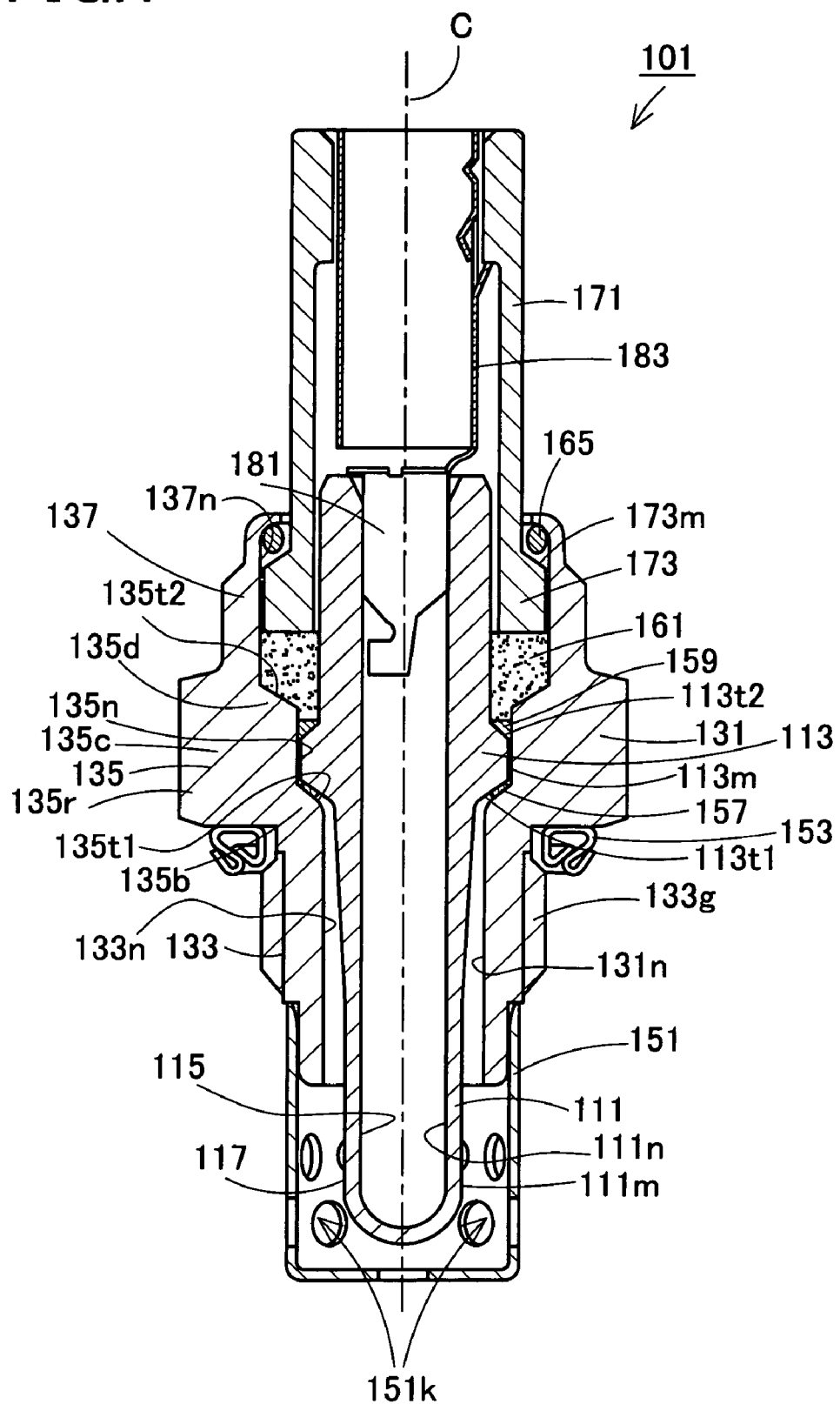
[FIG. 1] Sectional view of a gas sensor according to a first embodiment.

101, 301, 401: gas sensor
111, 311, 411: gas detection element
111*n*, 311*n*: inner circumferential surface (of gas detection element)
111*m*, 311*m*: outer circumferential surface (of gas detection element)
113, 313: projection (of gas detection element)
115, 315: inner electrode
117, 317: outer electrode
131, 331, 431: metallic shell
131*n*, 331*n*, 431*n*: inner circumferential surface (of metallic shell)
135*b*, 335*b*, 435*b*: stepped portion (of metallic shell)
157, 357, 457: plate packing (second packing)
159, 359, 459: first packing
165, 365, 465: wire packing
161, 361, 461: charged seal layer
421: element holder

BEST MODE FOR CARRYING OUT THE INVENTION (First Embodiment)

Embodiments of the present invention will next be described in detail with reference to the accompanying drawings.

Figure 2:
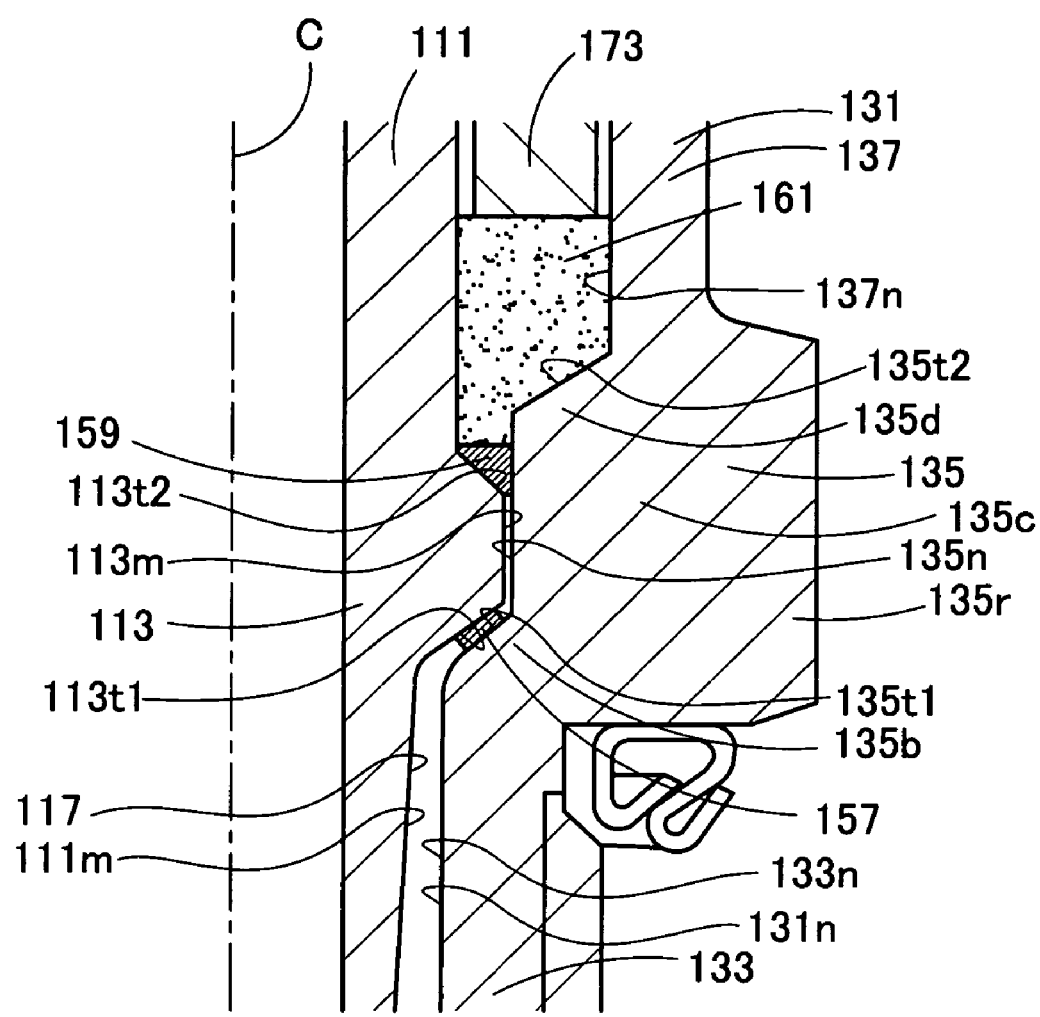
[FIG. 2] Partially enlarged sectional view of the gas sensor of the first embodiment, showing a region where a first packing and a plate packing are provided.
Figure 3:
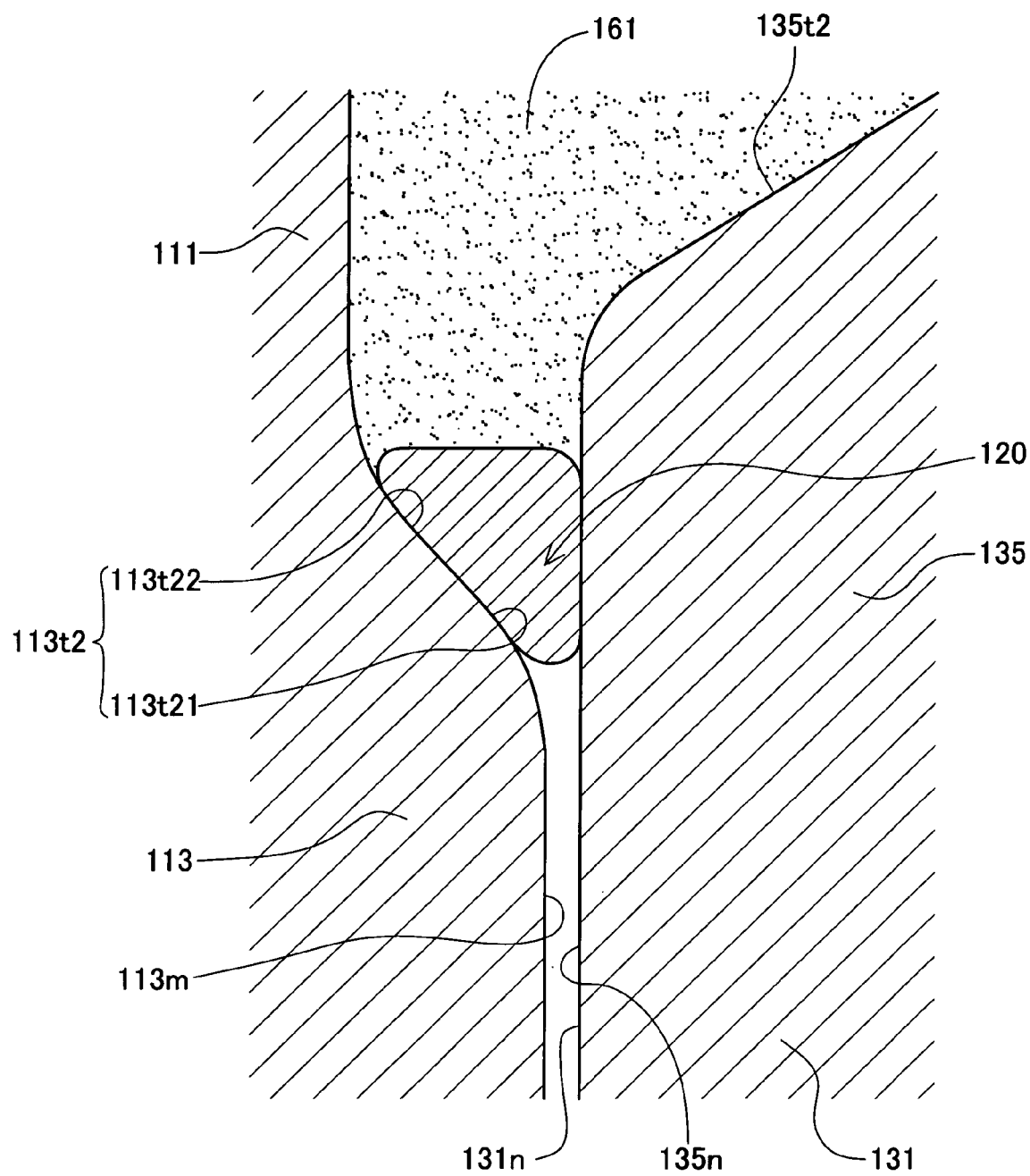
[FIG. 3] Partially enlarged sectional view of the gas sensor of the first embodiment, showing a main portion where the first packing is provided.

FIG. 1 is a sectional view of a gas sensor 101 of the present embodiment, and FIG. 2 is a partially enlarged sectional view of the gas sensor 101, showing a region where a first packing 159 and a plate packing (a second packing) 157 are provided. FIG. 3 is a partially enlarged sectional view of the gas sensor of the first embodiment, showing a main portion where the first packing 159 is provided. The gas sensor 101 is an oxygen sensor to be attached to an exhaust gas pipe of an internal combustion chamber in order to measure the oxygen concentration of exhaust gas. The gas sensor 101 includes a closed-bottomed tubular gas detection element (to-be-held member) 111 with the distal end (the lower end in FIG. 1) closed as viewed along the direction of the axis C, and a tubular metallic shell 131, which coaxially holds the gas detection element 111 therein.

The gas detection element 111 includes a projection 113, which is circumferentially formed at its central portion with respect to the direction of the axis C and projects radially outward. The projection 113 has a first tapered outer circumferential surface (a distal end surface (distal-end-side holding surface)) 113$t$1, which is located on its distal end and whose diameter increases from its distal end side toward its proximal end side; a second tapered outer circumferential surface (a proximal end surface (proximal-end-side holding surface)) 113$t$2, which is located on its proximal end and whose diameter increases from its proximal end side toward its distal end side; and a central outer circumferential surface 113$m$, which has a fixed diameter and connects the first tapered outer circumferential surface 113$t$1 and the second tapered outer circumferential surface 113$t$2. More specifically, as shown in FIG. 3, the second tapered outer circumferential surface (the proximal end surface (proximal-end-side holding surface)) 113$t$2 is composed of two curved surfaces; i.e., a first curved surface 113$t$21, which is located on the distal end side and is convex outward (rightward in FIG. 3), and a second curved surface 113$t$22, which is connected to the first curved surface 113$t$21, is located on the proximal end side, and is convex inward (leftward in FIG. 3). The gas detection element 111 is made from an oxygen-ion-conductive solid electrolyte; for example, a solid electrolyte that contains partially stabilized zirconia as a main component. The substantially entire inner circumferential surface 111$n$ of the gas sensor element 111 is clad with an inner electrode 115. An outer electrode 117 clads a portion of an outer circumferential surface 111$m$ that extends over the substantially entire surface of a distal end section of the gas detection element 111 projecting from the metallic shell 131. Furthermore, the outer electrode 117 clads a portion of the gas sensor element 111 that extends from the distal end portion of the gas sensor element 111 to the projection 113, in such a manner as to extend linearly in the axial direction. The inner electrodes 115 and the outer electrode 117 are made essentially of Pt.

The metallic shell 131 is made of stainless steel (SUS430) and composed of a distal end section 133 (a lower section in FIG. 1), a central section 135, and a proximal end section 137 (an upper section in FIG. 1). A through-hole whose wall is an inner circumferential surface 131$n$ extends through the metallic shell 131, and its diameter reduces from the proximal end of the metallic shell 131 to the distal end of the metallic shell 131.

The distal end section 133 has an inner circumferential surface 133$n$ having a relatively small diameter (about 6.5 mm), and a male-threaded portion 133$g$ formed on its outer circumference and adapted to attach the gas sensor 101 to an exhaust gas pipe. A protection cap 151 is attached to a distal end portion of the distal end section 133 for the purpose of protecting a distal end section of the gas detection element 111. The protection cap 151 is made of stainless steel; assumes a closed-bottomed tubular shape; and has a number of gas introduction holes 151$k$ for introducing exhaust gas into the interior of the gas sensor 101 from the exhaust pipe. A gasket 153 made of stainless steel is attached to a proximal end portion of the distal end section 133.

The central section 135 is composed of a first stepped portion 135$b$ having a first tapered inner circumferential surface (a support surface) 135$t$1, which is connected with the inner circumferential surface 133$n$ of the distal end section 133 and whose diameter increases toward the proximal end side of the gas sensor 101; a tubular portion 135$c$ having a central inner circumferential surface 135$n$, which is connected with the first tapered inner circumferential surface 135$t$1 and which has a diameter (about 9.1 mm) greater than that of the inner circumferential surface 133$n$; and a second stepped portion 135$d$ having a second tapered inner circumferential surface 135$t$2, which is connected with the central inner circumferential surface 135$n$ and whose diameter increases toward the proximal end side of the gas sensor 101. A radially outer portion of the central section 135 is formed into a hexagonal flange portion (a tool engagement portion) 135$r$, which is used in attaching the gas sensor 101 to the exhaust gas pipe.

The proximal end section 137 has an inner circumferential surface 137$n$, which is connected with the second tapered inner circumferential surface 135$t$2 of the central section 135 and which has a diameter (about 12.5 mm) greater than that of the central inner circumferential surface 135$n$.

An annular plate packing 157 made of metal (SUS430) and having a thickness of 0.3 mm is disposed on the first tapered inner circumferential surface 135$t$1 of the central section 135 of the metallic shell 131 and is in close contact with the first tapered inner circumferential surface 135$t$1. The first tapered outer circumferential surface 113$t$1 of the projection 113 of the gas detection element 111, which is coaxially inserted into the metallic shell 131, abuts the plate packing 157 from above. In other words, the first stepped portion 135$b$ of the central section 135 of the metallic shell 131 and the projection 113 of the gas detection element 111 are engaged via the plate packing 157. Thus, the plate packing 157 reliably establishes electrical connection between the metallic shell 131 and the outer electrode 117 of the gas detection element 111.

The C-type first packing 159 made of NW2201 (JIS H4551-2002), which contains Ni as a main component, is disposed on the proximal end side of the projection 113 of the inserted gas detection element 111 at such a position as to block a clearance between the projection 113 of the gas detection element 111 and the inner circumferential surface 131$n$ (the central inner circumferential surface 135$n$ of the central section 135) of the metallic shell 131. Specifically, the first packing 159 is disposed in an acute-angle clearance 120 formed by the second tapered outer circumferential surface 113$t$2 of the projection 113 and the central inner circumferential surface 135$n$ of the metallic shell 131 such that the first packing 159 has a wedge-like cross section and is in press contact with the second tapered outer circumferential surface 113*t*2 of the projection 113 and the central inner circumferential surface 135*n* of the metallic shell 131, respectively. More specifically, since a distal-end-side portion of the second tapered outer circumferential surface 113*t*2 of the projection 113 is formed by the first curved surface 113*t*21, a distal-end-side portion of the clearance 120 (see FIG. 3) assumes a shape such that the angle formed by the second tapered outer circumferential surface 113*t*2 of the projection 113 and the central inner circumferential surface 135*n* of the metallic shell 131 decreases toward the distal end. The first packing 159 extends to the portion where the above-mentioned angle deceases. Notably, although the first packing 159 is originally a wire packing having a diameter of about 0.6 mm, the wire packing is axially pressed toward the distal end side to thereby be plastically deformed such that the first packing 159 has a wedge-like cross section.

In a region located toward the proximal end of the gas sensor 101 with respect to the projection 113 (the first packing 159) of the gas detection element 111, a powder made essentially of talc is charged into an annular clearance provided between the outer circumferential surface 111*m* of a proximal end section of the gas detection element 111 and the inner circumferential surface 131*n* (the second tapered inner circumferential surface 135*t*2 of the central section 135 and the inner circumferential surface 137*n* of the proximal end section 137) of the metallic shell 131, thereby forming a charged seal layer 161.

In a region located toward the proximal end of the gas sensor 101 with respect to the charged seal layer 161, a distal end section 173 of a sleeve 171 is inserted into an annular clearance provided between the outer circumferential surface 111*m* of the gas detection element 111 and the inner circumferential surface 131*n* (the inner circumferential surface 137*n* of the proximal end section 137) of the metallic shell 131. The sleeve 171 is made of alumina. The distal end section 173 of the sleeve 171 assumes the form of a circumferential large-diameter portion projecting radially outward and has a tapered outer circumferential surface 173*m* whose diameter increases toward the distal end side of the distal end section 173. A wire packing 165 made of stainless steel (SUS430) is disposed on the tapered outer circumferential surface 173*m*. The tip end of the proximal end section 137 of the metallic shell 131 is bent radially inward in such a manner as to cover the second packing 165, thereby compressing the second packing 165 by means of crimping. The compressive crimping action axially compresses the charged seal layer 161, thereby coaxially holding the gas detection element 111 in the metallic shell 131. An elastic force (stress) of the charged seal layer 161 induced by the compressive crimping action enhances the performance of sealing the clearance between the outer circumferential surface 111*m* of the gas detection element 111 and the inner circumferential surface 131*n* of the metallic shell 131.

An element-side terminal 181 is inserted into the gas detection element 111 and electrically connected with the inner electrode 115 of the gas detection element 111. In order to output an output signal from the gas detection element 111 to an external device, the element-side terminal 181 is electrically connected to a sleeve-side terminal 183 formed in the sleeve 171. The element-side terminal 181 and the sleeve-side terminal 183 are made of an Ni alloy, such as INCONEL.

As described above, in the gas sensor 101 of the present embodiment, the first packing 159 is in press contact with the second tapered outer circumferential surface (the proximal end surface (proximal-end-side holding surface) 113*t*2 of the projection 113 of the gas detection element 111 and is also in press contact with the inner circumferential surface 131*n* (the central inner circumferential surface 135*n*) of the metallic shell 131. Thus, even when no external stress is exerted on the first packing 159, the first packing 159 can fix the gas detection element (to-be-held member) 111 in the metallic shell 131. Therefore, even when, as a result of long-term use of the gas sensor 101, loosening of the crimp or a like phenomenon occurs, the first packing 159 is less likely to become loose as compared with a conventional counterpart, and thus, positional shift of the gas detection element 111 is suppressed. Therefore, it is possible to suppress occurrence of defective contact between the plate packing (the second packing) 157 and the outer electrode 117 formed on the first tapered outer circumferential surface (the distal end surface) 113*t*1 of the projection 113 of the gas detection element 111 and between the plate packing (the second packing) 157 and the first tapered inner circumferential surface (the support surface) 135*t*1 of the first stepped portion 135*b* of the metallic shell 131. Thus, the reliability of electrical connection between the metallic shell 131 and the outer electrode 117 of the gas detection element 111 can be enhanced.

In particular, in the present embodiment, the first packing 159 is formed by axially pressing and plastically deforming a wire packing, which has been inserted into the clearance 120, such that the first packing 159 has a wedge-like cross section. Since the first packing 159 has a wedge-like cross section as a result of being strongly pressed and plastically deformed, the first packing 159 is strongly pressed against the second tapered outer circumferential surface 113*t*2 and the central inner circumferential surface 135*n*. Accordingly, the gas detection element 111 and the metallic shell 131 can be firmly fixed together.

Moreover, the distal-end-side portion of the clearance 120 assumes a shape (the first curved surface 113*t*21 in FIG. 3) such that the angle formed by the second tapered outer circumferential surface 113*t*2 and the inner circumferential surface 131*n* decreases toward the distal end, and the first packing 159 is disposed to extend to this portion. Therefore, the wedge effect increases toward the distal end of the first packing 159, so that the gas detection element 111 and the metallic shell 131 can be fixed together more firmly.

Furthermore, in the present embodiment, the charged seal layer 161 formed of a powder is provided in an annular clearance between the outer circumferential surface 111*m* of a proximal end section of the gas detection element 111 and the inner circumferential surface 131*n* (the second tapered inner circumferential surface 135*t*2 of the central section 135 and the inner circumferential surface 137*n* of the proximal end section 137) of the metallic shell 131, thereby enhancing the performance of sealing the clearance between the gas detection element 111 and the metallic shell 131.

Also, even when, as a result of long-term use of the gas sensor 101, loosening of the crimp or a like phenomenon occurs, the above-described structural feature of the first packing 159 suppresses occurrence of the following problem: particles of a powder pass through a clearance between the outer circumferential surface (the central outer circumference surface 113*m*) of the projection 113 of the gas detection element 111 and the inner circumferential surface (the central inner circumferential surface 135*n*) of the metallic shell 131 and reach a region where the plate packing 157 is provided; and the particles enter between the plate packing 157 and the gas detection element 111 or between the plate packing 157 and the metallic shell 131, causing defective contact therebetween.

Next, a method of manufacturing the above-described gas sensor 101 will be described.

First, the metallic shell 131, which has been manufactured by a known method in such a manner as to assume a predetermined shape, is prepared. Also, the gas detection element 111, which has been manufactured such that a solid electrolyte is clad with the inner electrode 115 and the outer electrode 117 and then fired by a known method, is prepared.

The plate packing 157 having a thickness of about 0.3 mm is inserted into the metallic shell 131 and disposed on the first tapered inner circumferential surface 135t1 of the stepped portion 135b of the central section 135 (the second-packing-inserting step).

Next, the gas detection element 111 is coaxially inserted into the metallic shell 131, and the first tapered outer circumferential surface 113t1 of the projection 113 of the gas detection element 111 is caused to abut the plate packing 157 (the element-inserting step).

Subsequently, a force of about 3 kN is axially imposed on the plate packing 157 and the gas detection element 111, thereby bringing the plate packing 157 in close contact with the first tapered inner circumferential surface 135t1 of the stepped portion 135b of the central section 135 (the second-packing-pressing step).

Figure 5:
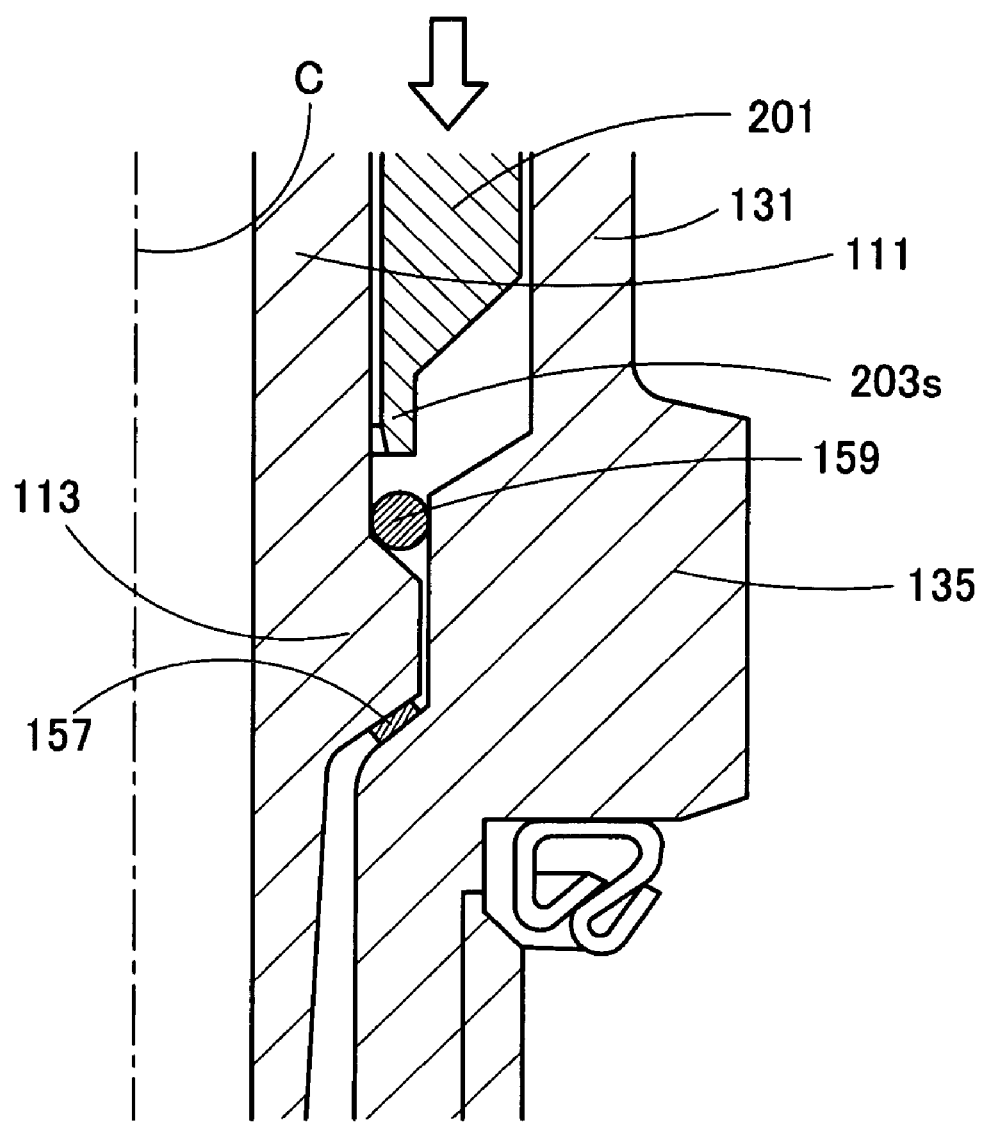
[FIG. 5] Explanatory view showing a manner of plastically deforming the wire packing in the method of manufacturing the gas sensor of the first embodiment.

Next, the wire packing 159, which is to become the first packing 159, is inserted into the metallic shell 131 into which the gas detection element 111 has been inserted, and is disposed on the proximal end side of the projection 113 of the gas detection element 111 and in a clearance (clearance 120) between the outer circumferential surface 111m of the gas detection element 111 and the inner circumferential surface 131n of the metallic shell 131 (the wire-packing-inserting step) (see FIG. 5).

Next, the wire packing 159 is axially pressed toward the distal end of the gas sensor 101 so as to be plastically deformed in the axial direction, thereby forming the first packing 159 (the first-packing-forming step). Specifically, as shown in FIG. 5, by use of a presser jig 201 shown in FIG. 4, the wire packing 159 is pressed axially toward the distal end of the gas sensor 101 as represented by the illustrated arrow with a force of about 5 kN. The presser jig 201 assumes a tubular shape and is composed of a distal end portion 203 having a small diameter and a proximal end portion 205 having a large diameter. The diameter of the distal end portion 203 is determined such that the distal end portion 203 can be inserted into a clearance between the outer circumferential surface 111m of a proximal end section of the gas detection element 111 and the inner circumferential surface 131n of the metallic shell 131. A distal end 203s of the distal end portion 203 is thin-walled so as to be able to press the wire packing 159. In the first-packing-forming step, the wire packing 159 is plastically deformed such that its cross-sectional shape changes from a circular shape to a wedge shape. As a result, the wire packing 159 abuts the second tapered outer circumferential surface 113t2 of the projection 113 of the gas detection element 111 and the central circumferential surface 135n of the central section 135 of the metallic shell 131.

Next, in order to form the charged seal layer 161, a powder that contains talc as a main component is charged into a clearance provided between the outer circumferential surface 111m of a proximal end section of the gas detection element 111 and the inner circumferential surface 131n of the metallic shell 131.

Subsequently, the distal end section 173 of the sleeve 171 is inserted into the above clearance. Then, the wire packing 165 is inserted and disposed on the tapered outer circumferential surface 173m of the distal end section 173 of the sleeve 171. The proximal end of the proximal end section 137 of the metallic shell 131 is bent radially inward, thereby performing compressive crimping in the axial direction.

Next, the element-side terminal 181 is inserted into the gas detection element 111 and brought into contact with the inner electrode 115 of the gas detection element 111. Also, the sleeve-side terminal 183 is inserted into the sleeve 171 and fixed therein. Subsequently, the protection cap 151 is attached to the distal end of the metallic shell 131. The gasket 153 is attached to a proximal end portion of the distal end section 133 of the metallic shell 131.

The gas sensor 101 is thus completed.

As described above, according to the method of manufacturing the gas sensor 101 of the present embodiment, in the second-packing-pressing step, the plate packing (the second packing) 157 is axially pressed to thereby be brought into close contact with the first tapered inner circumferential surface (the support surface) 135t1 of the stepped portion 135b of the metallic shell 131. Therefore, good contact is established between the plate packing 157 and the metallic shell 131.

In the first-packing-forming step, the wire packing 159 is axially pressed, to thereby be plastically deformed such that the wire packing (the first packing) 159 is pressed against the second tapered outer circumferential surface 113t2 of the projection 113 of the gas detection element 111 and the central inner circumferential surface 135n of the central section 135 of the metallic shell 131. Thus, even when no external stress is exerted on the first packing 159, the first packing 159 can fix the gas detection element (to-be-held member) 111 in the metallic shell 131. Therefore, even when, as a result of long-term use of the gas sensor 101, loosening of the crimp or a like phenomenon occurs, the first packing 159 is less likely to become loose as compared with a conventional counterpart, and positional shift of the gas detection element 111 is suppressed. Therefore, it is possible to suppress occurrence of defective contact between the plate packing 157 and the outer electrode 117 formed on the first tapered outer circumferential surface (the distal end surface) 113t1 of the projection 113 of the gas detection element 111 and between the plate packing 157 and the first tapered inner circumferential surface (the support surface) 135t1 of the first stepped portion 135b of the metallic shell 131. Thus, the reliability of electrical connection between the metallic shell 131 and the outer electrode 117 of the gas detection element 111 can be enhanced. Additionally, since the first packing 159 is formed as described above, the gas sensor 101 can be readily manufactured at low cost.

(Second Embodiment)

Next, a second embodiment of the present invention will be described with reference to the accompanying drawings. Description of structural features similar to those of the above-described first embodiment will be omitted or simplified.

Figure 6:
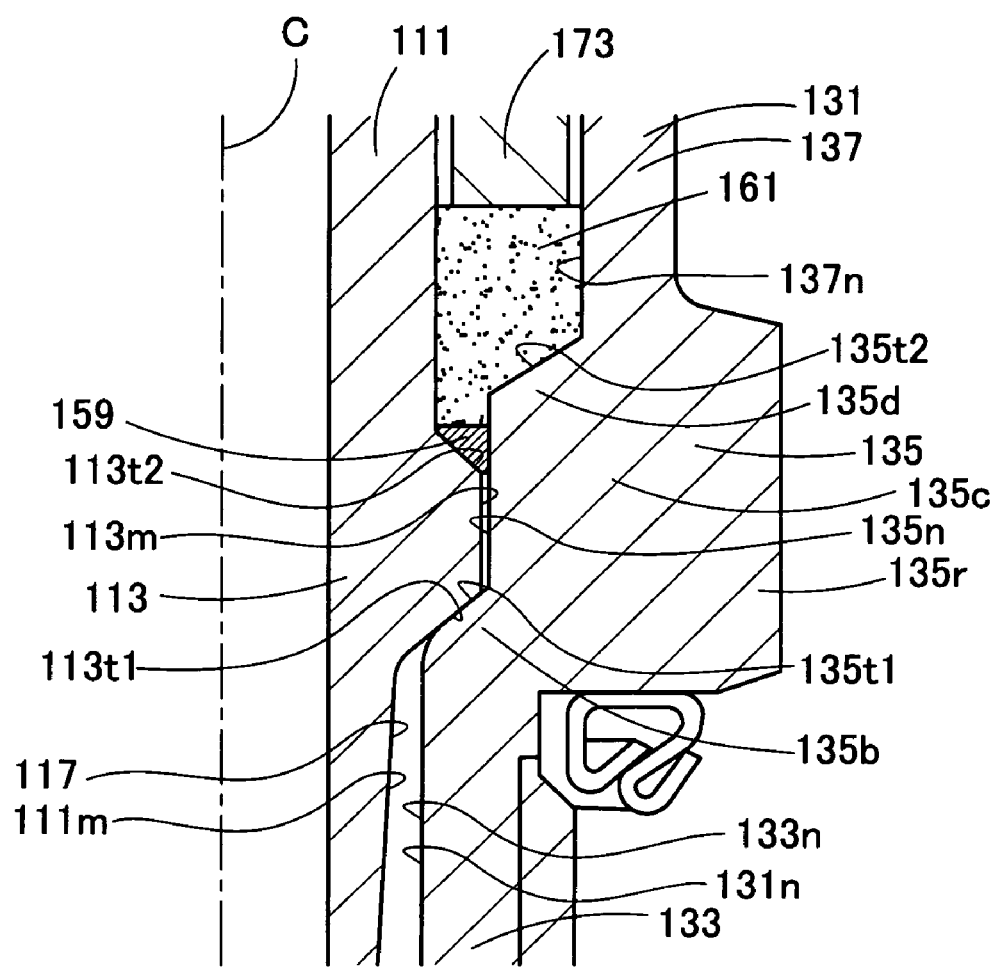
[FIG. 6] Partially enlarged sectional view of a gas sensor according to a second embodiment, showing a region where a first packing is provided.

FIG. 6 is a partially enlarged sectional view showing essential portions of a gas sensor according to the present embodiment. The gas sensor differs from that of the first embodiment in that the plate packing (the second packing) is eliminated. Other structural features are similar to those of the first embodiment and denoted by common reference numerals, and repeated description thereof is omitted.

In the present embodiment, no plate packing is provided on the first tapered inner circumferential surface 135t1 of the central section 135 of the metallic shell 131. In other words, the first stepped portion 135b of the central section 135 of the metallic shell 131 and the projection 113 of the gas detection element 111 are in direct contact with each other, thereby establishing direct electrical connection between the metallic shell 131 and the outer electrode 117 of the gas detection element 111.

Even in the present embodiment, the first packing 159 is strongly pressed against the second tapered outer circumferential surface (the proximal end surface (proximal-end-side surface)) 113*t*2 of the projection 113 of the gas detection element 111, and is strongly pressed against the inner circumferential surface 131*n* (the central inner circumferential surface 135*n*) of the metallic shell 131. Thus, even when no external stress is exerted on the first packing 159, the first packing 159 can fix the gas detection element (to-be-held member) 111 in the metallic shell 131. Therefore, even when, as a result of long-term use of the gas sensor 101, loosening of the crimp or a like phenomenon occurs, the first packing 159 is less likely to become loose as compared with a conventional counterpart, thereby suppressing positional shift of the gas detection element 111 and occurrence of defective contact between the plate packing 157 and the outer electrode 117 formed on the first tapered outer circumferential surface (the distal end surface) 113*t*1 of the projection 113 of the gas detection element 111 and between the plate packing 157 and the first tapered inner circumferential surface (the support surface) 135*t*1 of the first stepped portion 135*b* of the metallic shell 131. Thus, the reliability of electrical connection between the metallic shell 131 and the outer electrode 117 of the gas detection element 111 can be enhanced.

Other structural features similar to those of the first embodiment yield similar effects.

In a method of manufacturing the gas sensor of the present embodiment, steps regarding a plate packing is omitted, because the gas sensor of the present embodiment includes no plate packing. That is, after the metallic shell 131 and the gas detection element 111 are prepared, the element-inserting step is performed, without performance of the second-packing-inserting step. Next, the wire-packing-insertion step is performed, without performance of the second-packing-pressing step. Subsequently, as in the above-described first embodiment, the first-packing-forming step is performed. The remaining steps are performed in the same manner as in the first embodiment to thereby complete the gas sensor.

In the present embodiment as well, the first-packing-forming step is performed so as to form the first packing 159 into a wedge-like shape. Thus, even when no external stress is exerted on the first packing 159, the first packing 159 can fix the gas detection element (to-be-held member) 111 in the metallic shell 131. Therefore, even when, as a result of long-term use of the gas sensor 101, loosening of the crimp or a like phenomenon occurs, the first packing 159 is less likely to become loose as compared with a conventional counterpart, thereby suppressing positional shift of the gas detection element 111 and occurrence of defective contact between the outer electrode 117 formed on the first tapered outer circumferential surface (the distal end surface) 113*t*1 of the projection 113 of the gas detection element 111 and the first tapered inner circumferential surface (the support surface) 135*t*1 of the first stepped portion 135*b* of the metallic shell 131. Thus, the reliability of electrical connection between the metallic shell 131 and the outer electrode 117 of the gas detection element 111 can be enhanced. In addition, since the above-described first packing 159 is formed by plastically deforming a wire packing 159, the gas sensor can be easily manufactured at low cost.

(Third Embodiment)

Next, a third embodiment of the present invention will next be described in detail with reference to the accompanying drawings. Description of structural features similar to those of the above-described first or second embodiment will be omitted or simplified.

Figure 7:
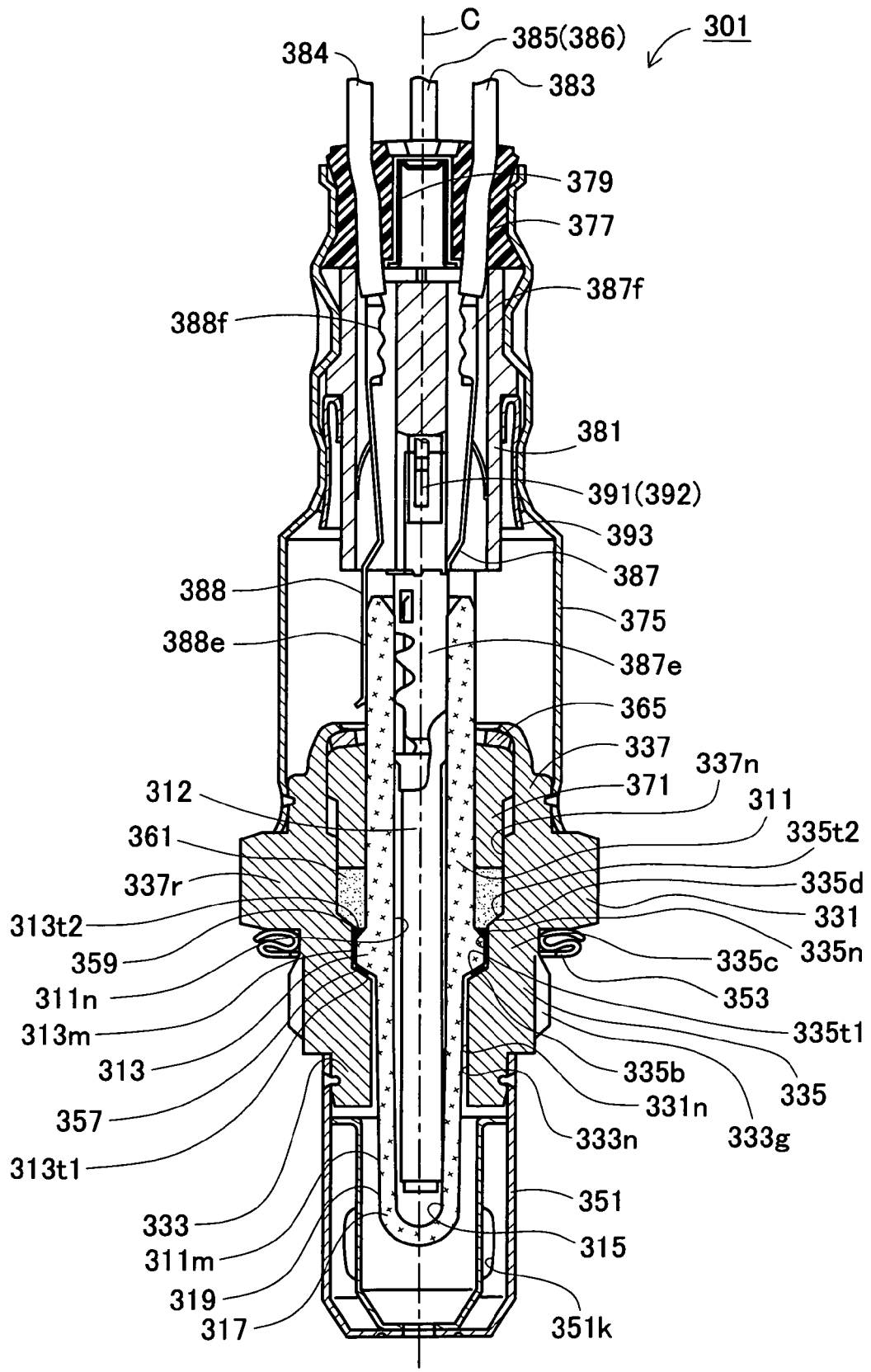
[FIG. 7] Sectional view of a gas sensor according to a third embodiment.
Figure 8:
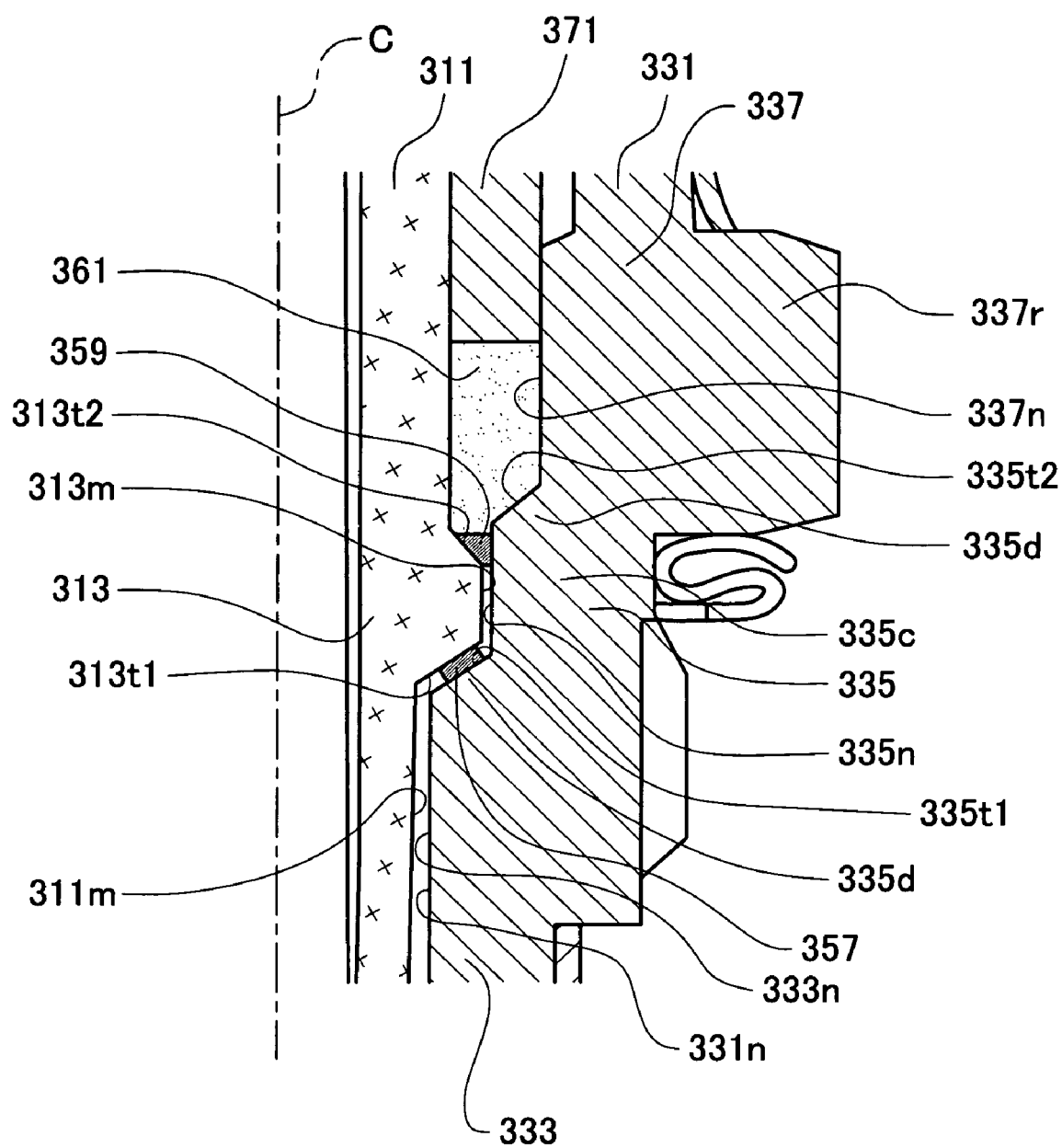
[FIG. 8] Partially enlarged sectional view of the gas sensor of the third embodiment, showing a region where a first packing and a plate packing are provided.
Figure 9:
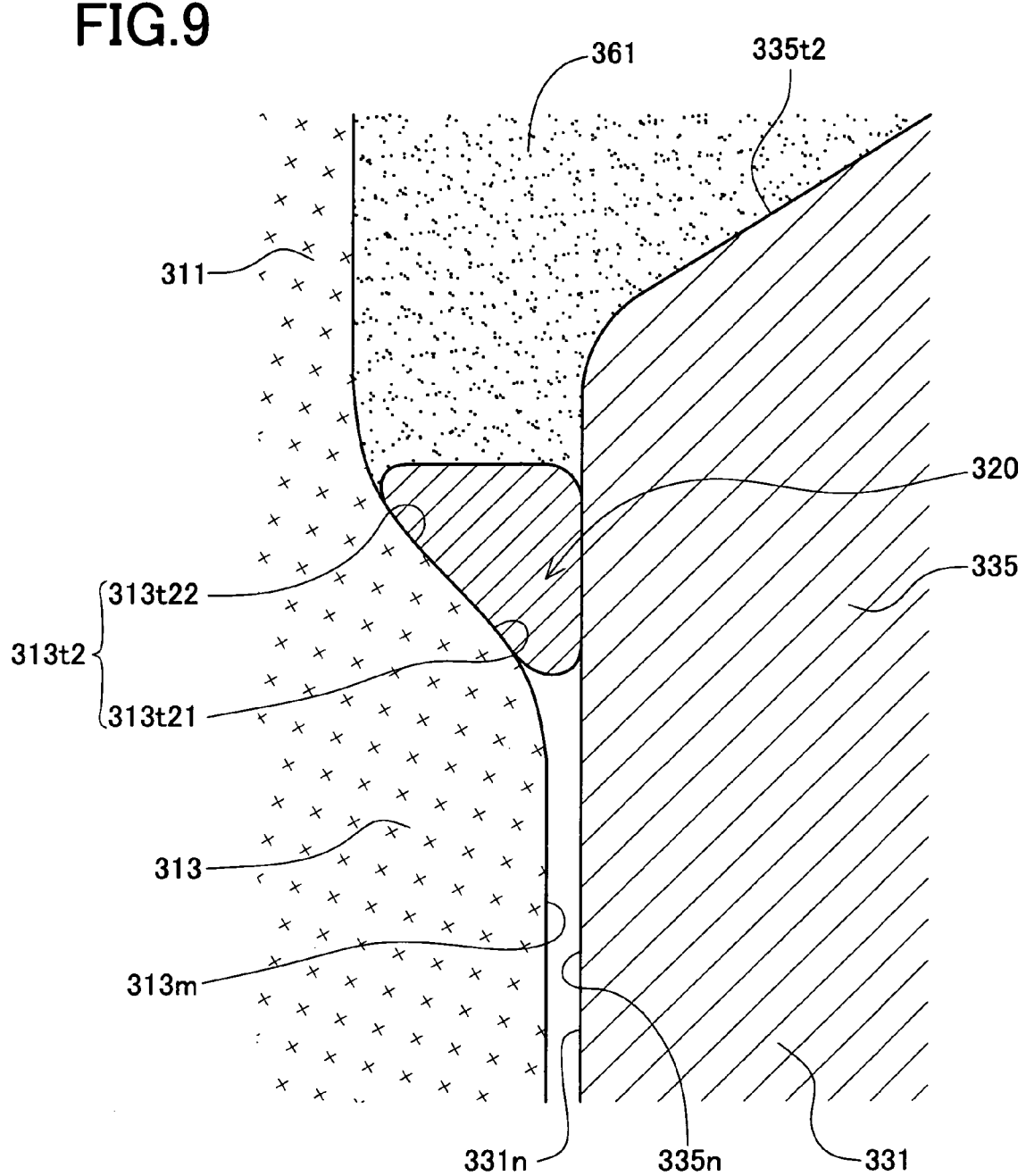
[FIG. 9] Partially enlarged sectional view of the gas sensor of the third embodiment, showing a main portion where the first packing is provided.

FIG. 7 is a sectional view of a gas sensor 301 of the present embodiment, and FIG. 8 is a partially enlarged sectional view of the gas sensor 301, showing a region where a first packing 359 and a plate packing (a second packing) 357 are provided. FIG. 9 is a partially enlarged sectional view of the gas sensor of the first embodiment, showing a main portion where the first packing 359 is provided. The gas sensor 301 is an oxygen sensor to be attached to an exhaust gas pipe of an internal combustion chamber in order to measure the oxygen concentration of exhaust gas. The gas sensor 301 includes a closed-bottomed tubular gas detection element (to-be-held member) 311 with the distal end (the lower end in FIG. 7) closed as viewed along the direction of the axis C, and a tubular metallic shell 331, which coaxially holds the gas detection element 311 therein.

The gas detection element 311 includes a projection 313, which is circumferentially formed at its central portion with respect to the direction of the axis C and projects radially outward. The projection 313 has a first tapered outer circumferential surface (a distal end surface (distal-end-side holding surface)) 313*t*1, which is located on its distal end and whose diameter increases from its distal end side toward its proximal end side; a second tapered outer circumferential surface (a proximal end surface (proximal-end-side holding surface)) 313*t*2, which is located on its proximal end and whose diameter increases from its proximal end side toward its distal end side; and a central outer circumferential surface 313*m*, which has a fixed diameter and connects the first tapered outer circumferential surface 313*t*1 and the second tapered outer circumferential surface 313*t*2. More specifically, as shown in FIG. 9, the second tapered outer circumferential surface (the proximal end surface (proximal-end-side holding surface)) 313*t*2 is composed of two curved surfaces; i.e., a first curved surface 313*t*21, which is located on the distal end side and is convex outward (rightward in FIG. 9), and a second curved surface 313*t*22, which is connected to the first curved surface 313*t*21, is located on the proximal end side, and is convex inward (leftward in FIG. 9). The gas detection element 311 is made from an oxygen-ion-conductive solid electrolyte; for example, a solid electrolyte that contains partially stabilized zirconia as a main component. The substantially entire inner circumferential surface 311*n* of the gas sensor element 311 is clad with an inner electrode 315. An outer electrode 317 clads a portion of an outer circumferential surface 311*m* that extends over the substantially entire surface of a distal end section of the gas detection element 311 projecting from the metallic shell 331. An insulative porous protection layer 319 is formed on the outer electrode 317. Notably, the inner electrodes 315 and the outer electrode 317 are made essentially of Pt. A heater 312 is inserted into the gas detection element 311. The heater 312 is a bar-shaped ceramic heater in which a heat generation portion including a resistant heating element is formed on a core material mainly formed of alumina.

The metallic shell 331 is made of stainless steel (SUS430) and composed of a distal end section 333 (a lower section in FIG. 7), a central section 335, and a proximal end section 337 (an upper section in FIG. 7). A through-hole whose wall is an inner circumferential surface 331*n* extends through the metallic shell 331, and its diameter reduces from the proximal end of the metallic shell 331 to the distal end of the metallic shell 331.

The distal end section 333 has an inner circumferential surface 333*n* having a relatively small diameter, and a male-threaded portion 333*g* formed on the outer circumferences of the distal end section 333 and a central section 335 to be described later, and adapted to attach the gas sensor 301 to an exhaust gas pipe. A protection cap 351 is attached to a distal end portion of the distal end section 333 for the purpose of protecting a distal end section of the gas detection element 311. The protection cap 351 is made of stainless steel; assumes a closed-bottomed tubular shape; and has a number of gas introduction holes 351*k* for introducing exhaust gas into the interior of the gas sensor 301 from the exhaust pipe.

The central section 335 is composed of a first stepped portion 335*b* having a first tapered inner circumferential surface (a support surface) 335*t*1, which is connected with the inner circumferential surface 333*n* of the distal end section 333 and whose diameter increases toward the proximal end side of the gas sensor 301; a tubular portion 335*c* having a central inner circumferential surface 335*n*, which is connected with the first tapered inner circumferential surface 335*t*1 and which has a diameter greater than that of the inner circumferential surface 333*n*; and a second stepped portion 335*d* having a second tapered inner circumferential surface 335*t*2, which is connected with the central inner circumferential surface 335*n* and whose diameter increases toward the proximal end side of the gas sensor 301. A gasket 353 made of stainless steel is attached to surround the central section 335.

The proximal end section 337 has an inner circumferential surface 337*n*, which is connected with the second tapered inner circumferential surface 335*t*2 of the central section 335 and which has a diameter greater than that of the central inner circumferential surface 335*n*. A radially outer portion of a distal end portion of the proximal end section 337 is formed into a hexagonal flange portion (a tool engagement portion) 337*r*, which is used in attaching the gas sensor 301 to the exhaust gas pipe.

An annular plate packing 357 (second packing) made of metal (SUS430) is disposed on the first tapered inner circumferential surface 335*t*1 of the central section 335 of the metallic shell 331 and is in close contact with the first tapered inner circumferential surface 335*t*1. The first tapered outer circumferential surface 313*t*1 of the projection 313 of the gas detection element 311, which is coaxially inserted into the metallic shell 331, abuts the plate packing 357 from above. In other words, the first stepped portion 335*b* of the central section 335 of the metallic shell 331 and the projection 313 of the gas detection element 311 are engaged via the plate packing 357.

The C-type first packing 359 made of NW2201 (JIS H4551-2002), which contains Ni as a main component, is disposed on the proximal end side of the projection 313 of the inserted gas detection element 311 at such a position as to block a clearance between the projection 313 of the gas detection element 311 and the inner circumferential surface 331*n* (the central inner circumferential surface 335*n* of the central section 335) of the metallic shell 331. Specifically, the first packing 359 is disposed in an acute-angle clearance 320 formed by the second tapered outer circumferential surface 313*t*2 of the projection 313 and the central inner circumferential surface 335*n* of the metallic shell 331 such that the first packing 359 has a wedge-like cross section and is in press contact with the second tapered outer circumferential surface 313*t*2 of the projection 313 and the central inner circumferential surface 335*n* of the metallic shell 331, respectively. More specifically, since a distal-end-side portion of the second tapered outer circumferential surface 313*t*2 of the projection 313 is formed by the first curved surface 313*t*21, a distal-end-side portion of the clearance 320 (see FIG. 9) assumes a shape such that the angle formed by the second tapered outer circumferential surface 313*t*2 and the central inner circumferential surface 335*n* decreases toward the distal end. The first packing 359 extends to the portion where the above-mentioned angle deceases. Notably, the first packing 359 is formed by axially pressing a wire packing toward the distal end side to thereby plastically deform it such that the first packing 359 has a wedge-like cross section.

In a region located toward the proximal end of the gas sensor 301 with respect to the projection 313 (the first packing 359) of the gas detection element 311, a powder made essentially of talc is charged into an annular clearance provided between the outer circumferential surface 311*m* of a proximal end section of the gas detection element 311 and the inner circumferential surface 331*n* (the second tapered inner circumferential surface 335*t*2 of the central section 335 and the inner circumferential surface 337*n* of the proximal end section 337) of the metallic shell 331, thereby forming a charged seal layer 361.

In a region located toward the proximal end of the gas sensor 301 with respect to the charged seal layer 361, a tubular insulator 371 made of alumina is inserted into an annular clearance provided between the outer circumferential surface 311*m* of the gas detection element 311 and the inner circumferential surface 331*n* (the inner circumferential surface 337*n* of the proximal end section 337) of the metallic shell 331. A second packing 365 made of stainless steel (SUS430) is disposed on the proximal end of the insulator 371. The tip end of the proximal end section 337 of the metallic shell 331 is bent radially inward in such a manner as to cover the second packing 365, thereby compressing the second packing 365 by means of crimping. The compressive crimping action axially compresses the charged seal layer 361, thereby coaxially holding the gas detection element 311 in the metallic shell 331. An elastic force (stress) of the charged seal layer 361 induced by the compressive crimping action enhances the performance of sealing the clearance between the outer circumferential surface 311*m* of the gas detection element 311 and the inner circumferential surface 331*n* of the metallic shell 331.

A tubular metal sleeve 375 is fixed to the proximal end section 337 of the metallic shell 331 from the outside by means of laser welding. A grommet 377 formed of rubber is fitted into a proximal-end-side opening of the metal sleeve 375 and is crimped. A filter member 379 which introduces air into the interior of the metal sleeve 375 and which prevents entry of water is disposed at a central portion of the grommet 377. A separator 381 formed of insulative alumina ceramic is provided on the distal end side of the grommet 377. Sensor output lead wires 383 and 384 and heater lead wires 385 and 386 are disposed such that they pass through the separator 381 and the grommet 377.

Further, connector portions 387*f* and 388*f* of sensor terminal metal pieces 387 and 388, which are electrically connected to the sensor output lead wires 383 and 384, and heater terminal members 391 and 392, which are electrically connected to the heater lead wires 385 and 386, are held in the separator 381, while being insulated from one another. Moreover, a proximal end portion of the heater 312 is inserted into the separator 381, and is held in a state in which the proximal end portion of the heater 312 is electrically connected to the heater terminal members 391 and 392. A distal end portion 387e of the sensor terminal metal piece 387 is inserted into the bottomed hole of the gas detection element 311, and is electrically connected to the inner electrode 315 of the gas detection element 311. A distal end portion 388e of the sensor terminal metal piece 388 is electrically connected to the outer electrode 317 formed on the outer circumference of the gas detection element 311.

Further, an urging metal piece 393 is disposed around the distal end portion of the separator 381 so as to urge the metal sleeve 375, and hold the separator 381 inside the metal sleeve 375.

As described above, in the gas sensor 301 of the present embodiment, the first packing 359 is strongly pressed against the second tapered outer circumferential surface (the proximal end surface (proximal-end-side holding surface) 313t2 of the projection 313 of the gas detection element 311 and is also strongly pressed against the inner circumferential surface 331n (the central inner circumferential surface 335n) of the metallic shell 331. Thus, even when no external stress is exerted on the first packing 359, the first packing 359 can fix the gas detection element (to-be-held member) 311 in the metallic shell 331. Therefore, even when, as a result of long-term use of the gas sensor 301, loosening of the crimp or a like phenomenon occurs, the first packing 359 is less likely to become loose as compared with a conventional counterpart, and thus, positional shift of the gas detection element 311 is suppressed.

In particular, in the present embodiment, the first packing 359 is formed by axially pressing and plastically deforming a wire packing, which has been inserted into the clearance 320, such that the first packing 359 has a wedge-like cross section. Since the first packing 359 has a wedge-like cross section as a result of being strongly pressed and plastically deformed, the first packing 359 is strongly pressed against the second tapered outer circumferential surface 313t2 and the central inner circumferential surface 335n. Accordingly, the gas detection element 311 and the metallic shell 331 can be firmly fixed together.

Moreover, the distal-end-side portion of the clearance 320 assumes a shape (the first curved surface 313t21 in FIG. 9) such that the angle formed by the second tapered outer circumferential surface 313t2 and the inner circumferential surface 331n decreases toward the distal end, and the first packing 359 is disposed to extend to this portion. Therefore, the wedge effect increases toward the distal end of the first packing 359, so that the gas detection element 311 and the metallic shell 331 can be fixed together more firmly.

Furthermore, in the present embodiment, the charged seal layer 361 formed of a powder is provided in an annular clearance between the outer circumferential surface 311m of a proximal end section of the gas detection element 311 and the inner circumferential surface 331n (the second tapered inner circumferential surface 335t2 of the central section 335 and the inner circumferential surface 337n of the proximal end section 337) of the metallic shell 331, thereby enhancing the performance of sealing the clearance between the gas detection element 311 and the metallic shell 331.

Also, even when, as a result of long-term use of the gas sensor 301, loosening of the crimp or a like phenomenon occurs, the above-described structural feature of the first packing 359 suppresses occurrence of the following problem: particles of a powder pass through a clearance between the outer circumferential surface (the central outer circumference 313m) of the projection 313 of the gas detection element 311 and the inner circumferential surface (the central inner circumferential surface 335n) of the metallic shell 331 and reach a region where the plate packing 357 is provided.

Next, a method of manufacturing the above-described gas sensor 301 will be described.

First, the metallic shell 331, which has been manufactured by a known method in such a manner as to assume a predetermined shape, is prepared. Also, the gas detection element 311, which has been manufactured such that a solid electrolyte is clad with the inner electrode 315 and the outer electrode 317 and then fired by a known method, is prepared.

The plate packing 357 is inserted into the metallic shell 331 and disposed on the first tapered inner circumferential surface 335t1 of the stepped portion 335b of the central section 335 (the second-packing-inserting step).

Next, the gas detection element 311 is coaxially inserted into the metallic shell 331, and the first tapered outer circumferential surface 313t1 of the projection 313 of the gas detection element 311 is caused to abut the plate packing 357 (the element-inserting step).

Subsequently, a force of about 3 kN is axially imposed on the plate packing 357 and the gas detection element 311, thereby bringing the plate packing 357 in close contact with the first tapered inner circumferential surface 335t1 of the stepped portion 335b of the central section 335 (the second-packing-pressing step).

Next, the wire packing 359, which is to become the first packing 359, is inserted into the metallic shell 331 into which the gas detection element 311 has been inserted, and is disposed on the proximal end side of the projection 313 of the gas detection element 311 and in a clearance (clearance 320) between the outer circumferential surface 311m of the gas detection element 311 and the inner circumferential surface 331n of the metallic shell 331 (the wire-packing-inserting step).

Figure 4:
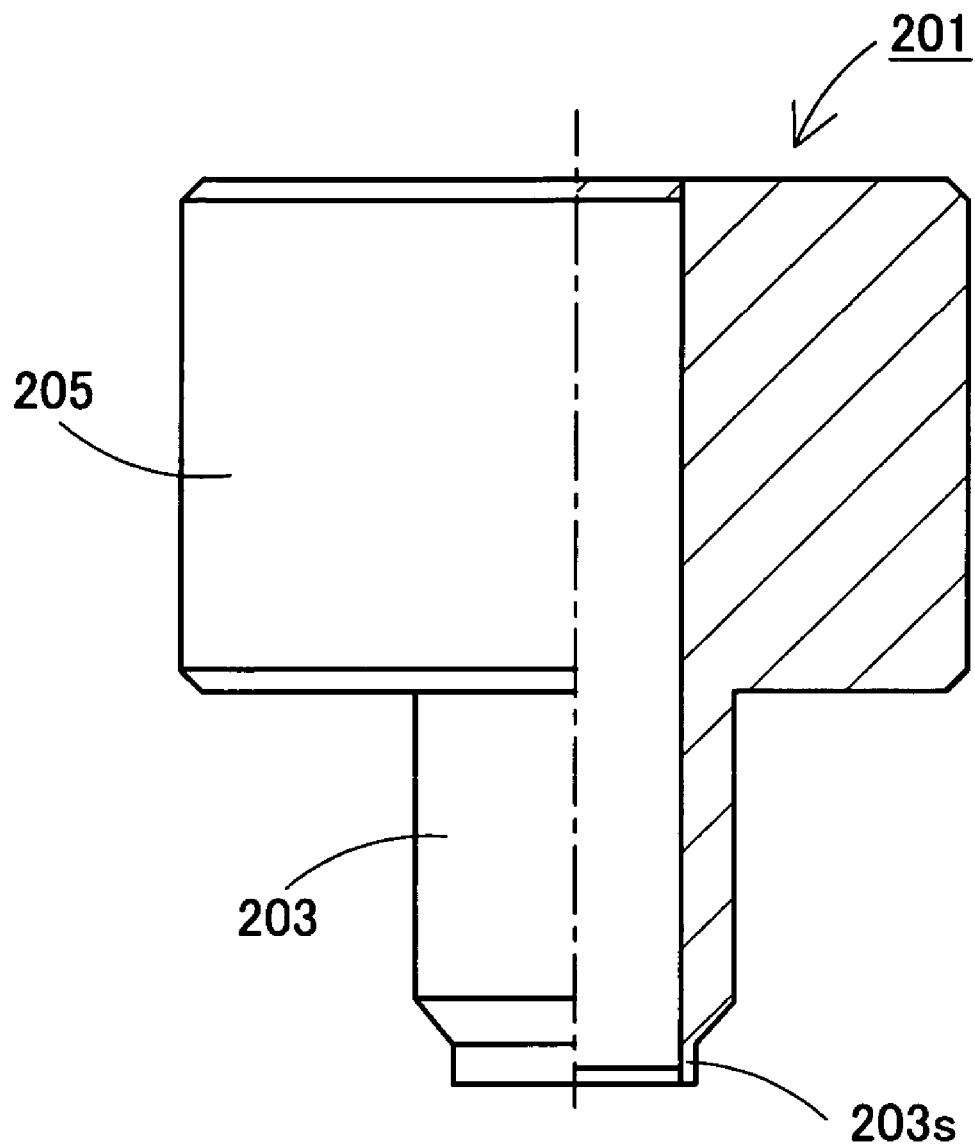
[FIG. 4] Explanatory view showing a presser jig for pressing a wire packing in a method of manufacturing the gas sensor of the first embodiment.

Next, the wire packing 359 is axially pressed toward the distal end of the gas sensor 301 so as to be plastically deformed in the axial direction, thereby forming the first packing 359 (the first-packing-forming step). Specifically, by use of a presser jig as shown in FIG. 4, the wire packing 359 is pressed axially toward the distal end of the gas sensor 301 with a force of about 5 kN. Thus, the wire packing 359 is plastically deformed such that its cross-sectional shape changes from a circular shape to a wedge shape, and is strongly pressed against the second tapered outer circumferential surface 313t2 of the projection 313 of the gas detection element 311 and the central inner circumferential surface 335n of the central section 335 of the metallic shell 331.

Next, in order to form the charged seal layer 361, a powder that contains talc as a main component is charged into a clearance provided between the outer circumferential surface 311m of a proximal end section of the gas detection element 311 and the inner circumferential surface 331n of the metallic shell 331.

Subsequently, the insulator 371 is inserted into the above clearance, and is axially pressed. Then, the wire packing 365 is inserted, and the tip end of the proximal end section 337 of the metallic shell 331 is bent radially inward, thereby performing compressive crimping in the axial direction. Further, the protection cap 351 is attached to the distal end of the metallic shell 331, and the gasket 353 is attached to the metallic shell 331.

Meanwhile, the sensor output leads 383 and 384 are connected to the sensor terminal metal pieces 387 and 388, and the heater lead wires 385 and 386 are connected to the heater terminal metal pieces 391 and 392. These are inserted into the separator 381, and the proximal end portion of the heater 312 is also inserted into the separator 381. Further, the urging metal piece 387 is attached to the outer circumference of the separator 381. After that, the separator 381 and the grommet 377 are inserted into the metal sleeve 375 with play.

Next, the metal sleeve 375, which includes the separator 381, etc., is brought into engagement of a predetermined portion of the metallic shell 331, into which the gas detection element 311 has been assembled. After that, a distal-end-side portion of the metal sleeve 375 is crimpled so as to provisionally couple the metal sleeve 375 and the metallic shell 331.

Next, a proximal-end-side portion of the metal sleeve 375 is deformed such that its diameter decreases, whereby the separator 381, etc. are fixed within the metal sleeve 375. Further, a further proximal-end-side portion of the metal sleeve 375 is crimped so as to fix the grommet 377. After that, the metal sleeve 375 and the metallic shell 331, having been provisionally coupled, is fixed together by means of laser welding.

Thus, the gas sensor 301 is completed.

As described above, according to the method of manufacturing the gas sensor 301 of the present embodiment, in the second-packing-pressing step, the plate packing (the second packing) 357 is axially pressed to thereby be brought into close contact with the first tapered inner circumferential surface (the support surface) 335$t$1 of the stepped portion 335$b$ of the metallic shell 331. Therefore, good contact is established between the plate packing 357 and the metallic shell 331.

In the first-packing-forming step, the wire packing 359 is axially pressed, to thereby be plastically deformed such that the wire packing (the first packing) 359 is strongly pressed against the second tapered outer circumferential surface 313$t$2 of the projection 313 of the gas detection element 311 and the central inner circumferential surface 335$n$ of the central section 335 of the metallic shell 331. Thus, even when no external stress is exerted on the first packing 359, the first packing 359 can fix the gas detection element (to-be-held member) 311 in the metallic shell 331. Therefore, even when, as a result of long-term use of the gas sensor 301, loosening of the crimp or a like phenomenon occurs, the first packing 359 is less likely to become loose as compared with a conventional counterpart, and positional shift of the gas detection element 311 is suppressed. Additionally, since the above-described first packing 359 is formed by plastically deforming a wire packing 359, the gas sensor 301 can be easily manufactured at low cost.

(Fourth Embodiment)

Next, a fourth embodiment of the present invention will next be described in detail with reference to the accompanying drawings. Description of structural features similar to those of the above-described first to third embodiments will be omitted or simplified.

Figure 10:
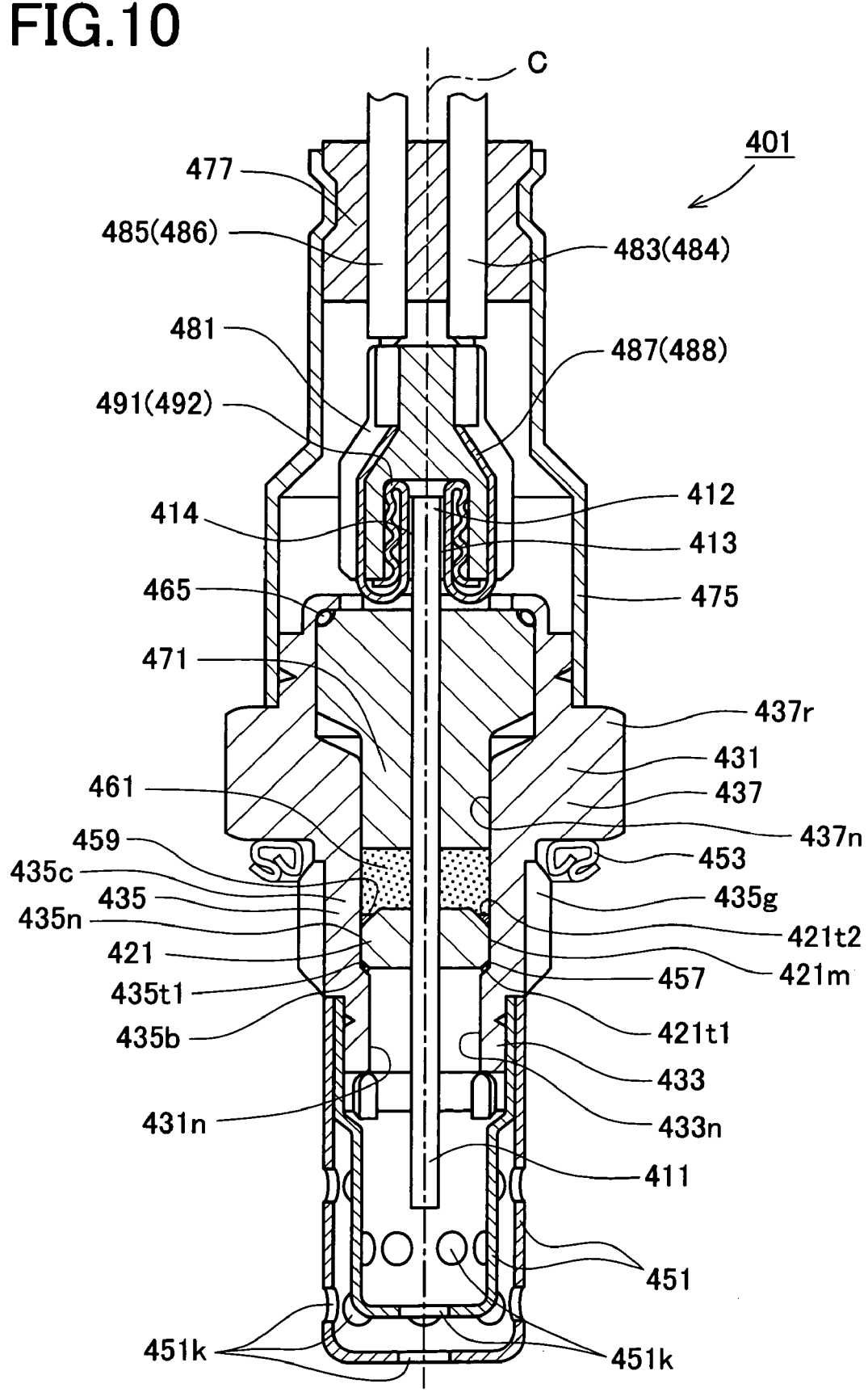
[FIG. 10] Sectional view of a gas sensor according to a fourth embodiment.
Figure 11:
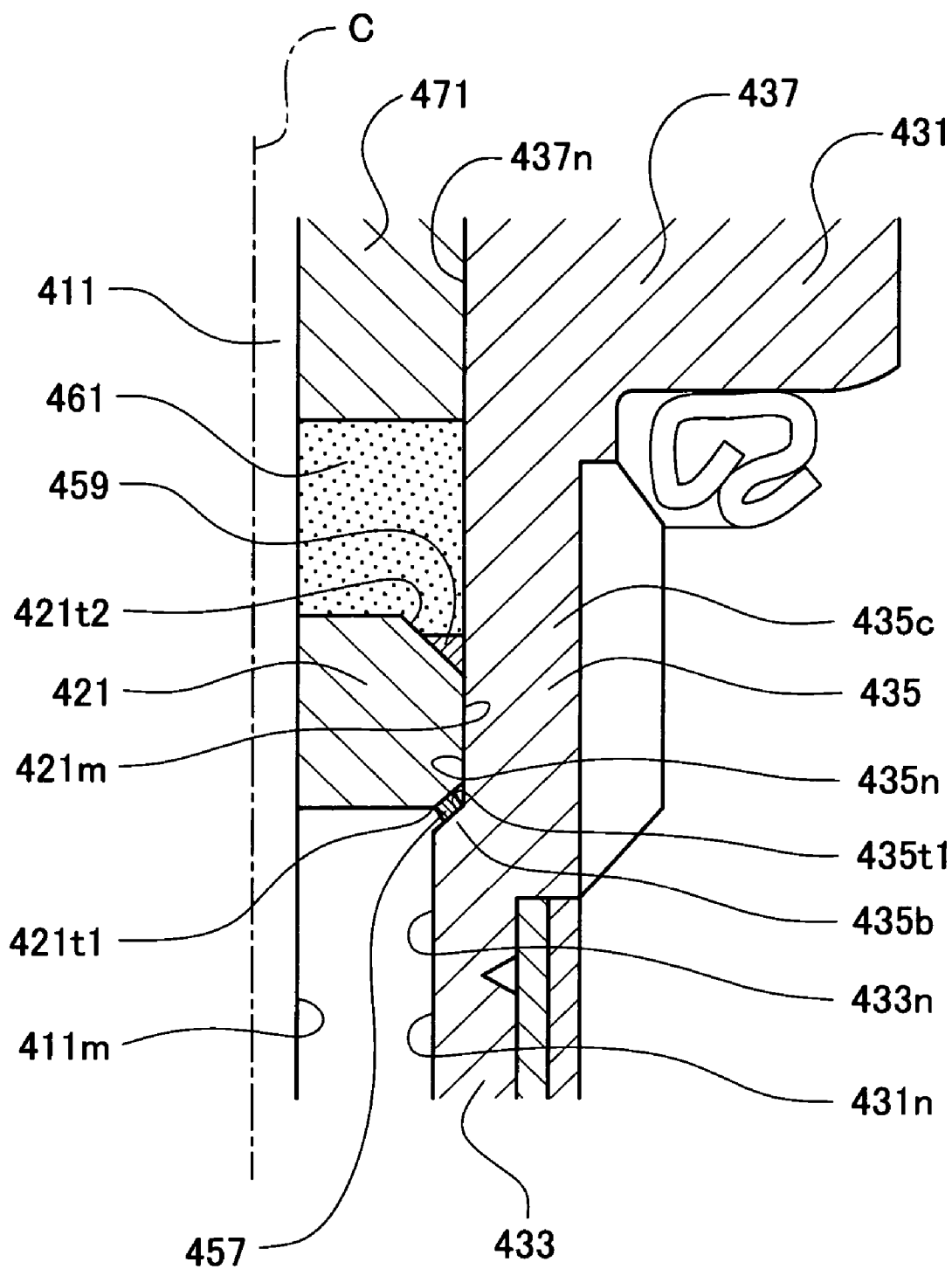
[FIG. 11] Partially enlarged sectional view of the gas sensor of the fourth embodiment, showing a region where a first packing and a plate packing are provided.
Figure 12:
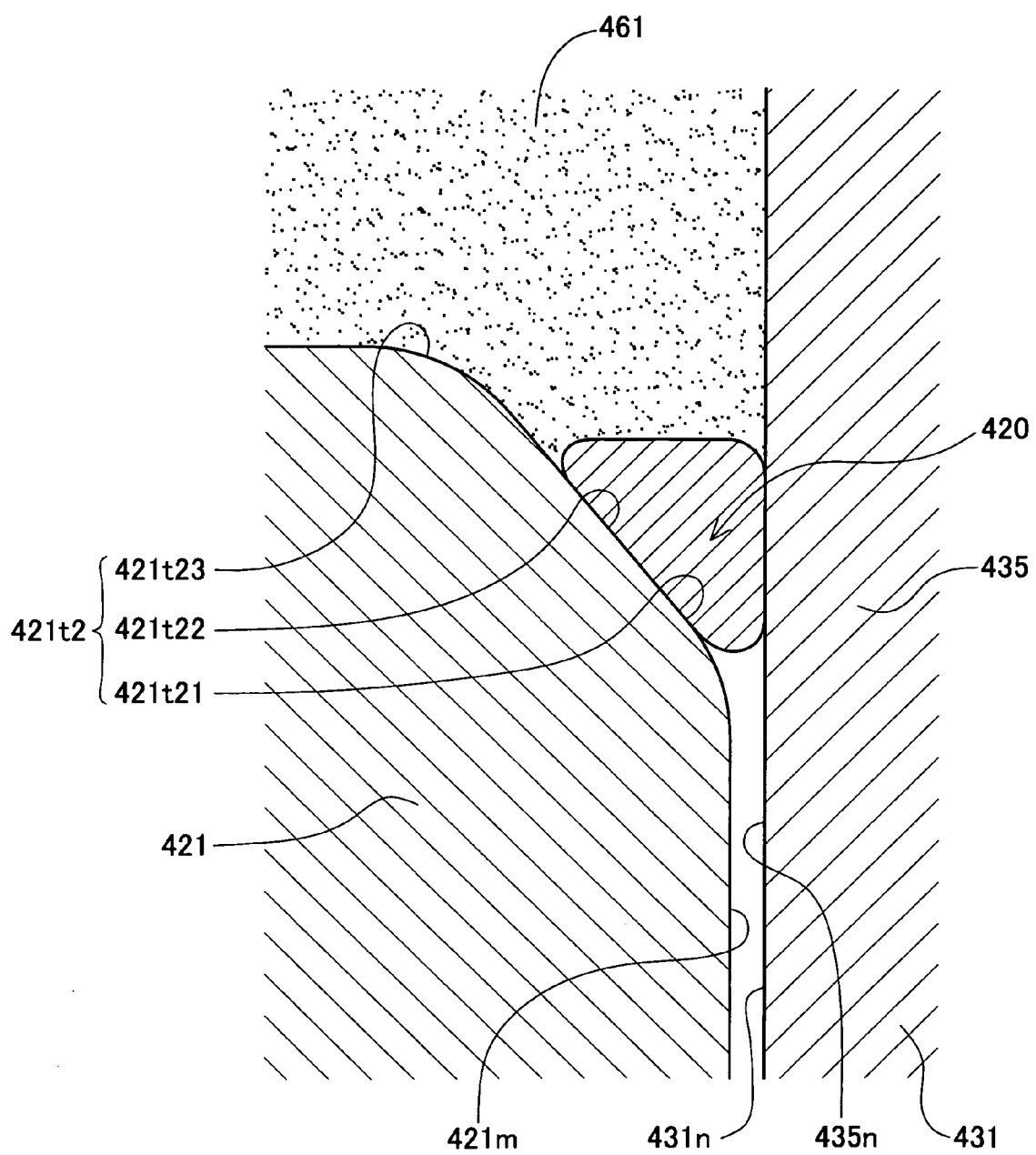
[FIG. 12] Partially enlarged sectional view of the gas sensor of the fourth embodiment, showing a main portion where the first packing is provided.
Figure 13:
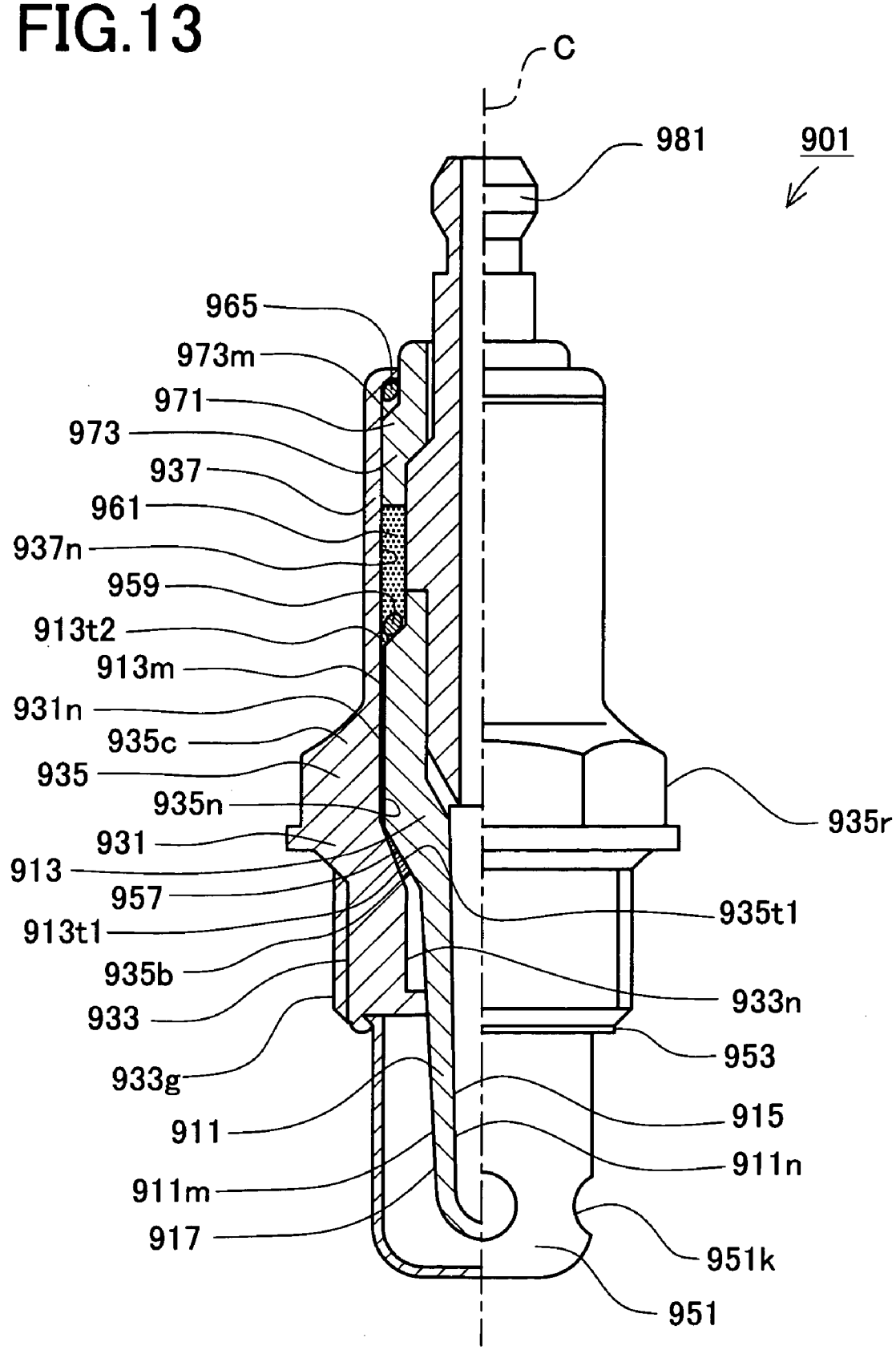
[FIG. 13] Partial sectional view of a conventional gas sensor.

FIG. 10 is a sectional view of a gas sensor 401 of the present embodiment, and FIG. 11 is a partially enlarged sectional view of the gas sensor 401, showing a region where a first packing 459 and a plate packing (a second packing) 457 are provided. FIG. 12 is a partially enlarged sectional view of the gas sensor of the first embodiment, showing a main portion where the first packing 459 is provided. The gas sensor 401 is an oxygen sensor to be attached to an exhaust gas pipe of an internal combustion chamber in order to measure the oxygen concentration of exhaust gas. The gas sensor 401 includes a bar-shaped gas detection element 411 extending along the direction of the axis C, a tubular element holder (to-be-held member) 421 having an opening through which the gas detection element 411 passes through, and a tubular metallic shell 431, which holds the element holder 421 therein.

The gas detection element 411 is mainly formed of ceramic, and has gas-sensitive characteristics which enable measurement of oxygen concentration within a gas to be measured. The gas detection element 411 includes an elongated-plate shaped oxygen concentration cell element and an elongated-plate shaped heater, which are layered together. The oxygen concentration cell element has a measurement electrode formed on a surface of a solid electrolyte layer (surface exposed to the gas to be measured) and a reference electrode formed on the reverse surface. The heater includes a heat generating resistor provided therein in order to activate the oxygen concentration cell element. The gas detection element 411 has a rectangular cross section taken perpendicular to the axial direction. A plurality of (two) electrode terminals 413 are formed on one of opposite surfaces of a rear end portion 412 of the sensor element 411, and are electrically connected to the measurement electrode and the reference electrode, respectively, via leads, so as to output electromotive force generated in the oxygen concentration cell element. A plurality of (two) electrode terminals 414 are formed on the other surface so as to supply electrical power to the heat generating resistor of the heater. These electrode terminals 413 and 414 are mainly formed of Pt.

The element holder 421 has a first tapered outer circumferential surface (a distal end surface (distal-end-side holding surface)) 421$t$1, which is located on its distal end of the outer circumference and whose diameter increases from its distal end side toward its proximal end side; a second tapered outer circumferential surface (a proximal end surface (proximal-end-side holding surface)) 421$t$2, which is located on its proximal end of the outer circumference and whose diameter increases from its proximal end side toward its distal end side; and an outer circumferential surface 421$m$ which connects these surfaces and which has a constant diameter. The element holder 421 is formed of insulative ceramic. More specifically, as shown in FIG. 12, the second tapered outer circumferential surface (the proximal end surface (proximal-end-side holding surface)) 421$t$2 is composed of two curved surfaces and a single flat surface; i.e., a first curved surface 421$t$21, which is located on the distal end side and is convex outward (rightward in FIG. 12), a second curved surface 421$t$23, which is located on the proximal end side and is convex inward (leftward in FIG. 12), and a flat surface 421$t$22, which connects these surfaces.

The metallic shell 431 is made of stainless steel (SUS430) and composed of a distal end section 433 (a lower section in FIG. 10), a central section 435, and a proximal end section 437 (an upper section in FIG. 10). A through-hole whose wall is an inner circumferential surface 431$n$ extends through the metallic shell 431, and its diameter reduces from the proximal end of the metallic shell 431 to the distal end of the metallic shell 431.

The distal end section 433 has an inner circumferential surface 433$n$ having a relatively small diameter. A double-wall protection cap 451 is attached to a distal end portion of the distal end section 433 for the purpose of protecting a distal end section of the gas detection element 411. The protection cap 451 is made of stainless steel; assumes a closed-bottomed tubular shape; and has a number of gas introduction holes 451$k$ for introducing exhaust gas into the interior of the gas sensor 401 from the exhaust pipe.

The central section 435 is composed of a first stepped portion 435b having a first tapered inner circumferential surface (a support surface) 435t1, which is connected with the inner circumferential surface 433n of the distal end section 433 and whose diameter increases toward the proximal end side of the gas sensor 401; and a tubular portion 435c having an inner circumferential surface 435n, which is connected with the first tapered inner circumferential surface 435t1 and which has a diameter greater than that of the inner circumferential surface 433n. A male-threaded portion 435g is formed on the outer circumferences of the central section 435, and adapted to attach the gas sensor 401 to an exhaust gas pipe.

The proximal end section 437 has an inner circumferential surface 437n, which is connected with the inner circumferential surface 435n of the central section 435. A gasket 453 formed of stainless steel is attached to the outer circumference of a distal-end-side portion of the proximal end section 437. A remaining portion of the proximal end section 437 located on the proximal end side of the gasket 453 is formed into a hexagonal flange portion (a tool engagement portion) 437r, which is used in attaching the gas sensor 401 to the exhaust gas pipe.

An annular plate packing 457 (second packing) made of metal (SUS430) is disposed on the first tapered inner circumferential surface 435t1 of the central section 435 of the metallic shell 431 and is in close contact with the first tapered inner circumferential surface 435t1. The first tapered outer circumferential surface 421t1 of the element holder 421, which is coaxially inserted into the metallic shell 431, abuts the plate packing 457 from above. In other words, the first stepped portion 435b of the central section 435 of the metallic shell 431 and the element holder 421 are reliably engaged via the plate packing 457 in a surface-to-surface contact relation.

The C-type first packing 459 made of NW2201 (JIS H4551-2002), which contains Ni as a main component, is disposed on the proximal end side of the inserted element holder 421 at such a position as to block a clearance between the element holder 421 and the inner circumferential surface 431n (the central inner circumferential surface 435n of the central section 435) of the metallic shell 431. Specifically, the first packing 459 is disposed in an acute-angle clearance 420 (see FIG. 12) formed by the second tapered outer circumferential surface 421t1 of the element holder 421 and the central inner circumferential surface 435n of the metallic shell 431 such that the first packing 459 has a wedge-like cross section and is strongly pressed against the second tapered outer circumferential surface 421t2 of the element holder 421 and the central inner circumferential surface 435n of the metallic shell 431, respectively. More specifically, since a distal-end-side portion of the second tapered outer circumferential surface 421t2 is formed by the curved first curved surface 421t21, a distal-end-side portion of the clearance 420 assumes a shape such that the angle formed by the second tapered outer circumferential surface 421t2 and the central inner circumferential surface 435n decreases toward the distal end. The first packing 459 extends to the portion where the above-mentioned angle deceases. Notably, the first packing 459 is formed by axially pressing a wire packing toward the distal end side to thereby plastically deform it such that the first packing 459 has a wedge-like cross section.

In a region located toward the proximal end of the gas sensor 401 with respect to the element holder 421 (the first packing 459) of the gas detection element 411, a powder made essentially of talc is charged into an annular clearance provided between the outer circumferential surface 411m of the gas detection element 411 and the inner circumferential surface 431n of the metallic shell 431, thereby forming a charged seal layer 461.

In a region located toward the proximal end of the gas sensor 401 with respect to the charged seal layer 461, a tubular insulator 471 made of alumina is inserted into an annular clearance provided between the outer circumferential surface 411m of the gas detection element 411 and the inner circumferential surface 431n (the inner circumferential surface 437n of the proximal end section 437) of the metallic shell 431. A second packing 465 made of stainless steel (SUS430) is disposed on the proximal end of the tubular insulator 471. The tip end of the proximal end section 437 of the metallic shell 431 is bent radially inward in such a manner as to cover the second packing 465, thereby compressing the second packing 465 by means of crimping. The compressive crimping action axially compresses the charged seal layer 461, thereby coaxially holding the element holder 421 in the metallic shell 431. An elastic force (stress) of the charged seal layer 461 induced by the compressive crimping action enhances the performance of sealing the clearance between the outer circumferential surface 421m of the element holder 421 and the inner circumferential surface 431n of the metallic shell 431.

A tubular metal sleeve 475 is fixed to the proximal end section 437 of the metallic shell 431 from the outside by means of laser welding. A grommet 477 formed of rubber is fitted into a proximal-end-side opening of the metal sleeve 475 and is crimped. Sensor output lead wires 483 and 484 and heater lead wires 485 and 486 pass through the grommet 477.

A separator 481 formed of insulative alumina ceramic is provided on the distal end side of the grommet 477. Sensor terminal metal pieces 487 and 488, which are electrically connected to the sensor output lead wires 483 and 484, and heater terminal metal pieces 491 and 492, which are electrically connected to the heater lead wires 485 and 486, are held in the separator 481, while being insulated from one another. Moreover, a proximal end portion 412 of the gas detection element 411 is inserted into the separator 481, and is held in a state in which the electrode terminals 413 and 414 formed on the proximal end portion 412 are electrically connected to the sensor terminal metal pieces 487 and 488 and the heater terminal metal pieces 491 and 492.

As described above, in the gas sensor 401 of the present embodiment, the first packing 459 is strongly pressed against the second tapered outer circumferential surface (the proximal end surface (proximal-end-side holding surface) 421t2 of the element holder 421 and is also strongly pressed against the inner circumferential surface 431n (the central inner circumferential surface 435n) of the metallic shell 431. Thus, even when no external stress is exerted on the first packing 459, the first packing 459 can fix the element holder (to-be-held member) 421 in the metallic shell 431. Therefore, even when, as a result of long-term use of the gas sensor 401, loosening of the crimp or a like phenomenon occurs, the first packing 459 is less likely to become loose as compared with a conventional counterpart, and thus, positional shift of the element holder 421 is suppressed.

In particular, in the present embodiment, the first packing 459 is formed by axially pressing and plastically deforming a wire packing, which has been inserted into the clearance 420, such that the first packing 459 has a wedge-like cross section. Since the first packing 459 has a wedge-like cross section as a result of being strongly pressed and plastically deformed, the first packing 459 is strongly pressed against the second tapered outer circumferential surface 421*t*2 and the central inner circumferential surface 435*n*. Accordingly, the element holder 421 and the metallic shell 431 can be firmly fixed together.

Moreover, the distal-end-side portion of the clearance 420 assumes a shape (the first curved surface 421*t*21 in FIG. 12) such that the angle formed by the second tapered outer circumferential surface 421*t*2 and the central inner circumferential surface 435*n* decreases toward the distal end, and the first packing 459 is disposed to extend to this portion. Therefore, the wedge effect increases toward the distal end of the first packing 459, so that the element holder 421 and the metallic shell 431 can be fixed together more firmly.

Furthermore, in the present embodiment, the charged seal layer 461 formed of a powder is provided on the proximal end side of the first packing 459 and in the annular clearance between the outer circumferential surface 411*m* of the gas detection element 411 and the inner circumferential surface 431*n* of the metallic shell 431, thereby enhancing the performance of sealing the clearance between the gas detection element 411 and the metallic shell 431.

Also, even when, as a result of long-term use of the gas sensor 401, loosening of the crimp or a like phenomenon occurs, the above-described structural feature of the first packing 459 suppresses occurrence of the following problem: particles of a powder pass through the clearance between the outer circumferential surface (the outer circumference 421*m*) of the element holder 421 and the inner circumferential surface (the central inner circumferential surface 435*n*) of the metallic shell 431 and reach a region where the plate packing 457 is provided.

Next, a method of manufacturing the above-described gas sensor 401 will be described.

First, the metallic shell 431, which has been manufactured by a known method in such a manner as to assume a predetermined shape, is prepared. Also, the gas detection element 411, which has been manufactured by a known method, is prepared.

The plate packing 457 is inserted into the metallic shell 431 and disposed on the first tapered inner circumferential surface 435*t*1 of the stepped portion 435*b* of the central section 435 (the second-packing-inserting step).

Next, the element holder 421, into which the gas detection element 411 has been inserted, is coaxially inserted into the metallic shell 431, and the first tapered outer circumferential surface 421*t*1 of the element holder 421 is caused to abut the plate packing 457 (the element-holder-inserting step).

Subsequently, a force of about 3 kN is axially imposed on the plate packing 457 and the element holder 421, thereby bringing the plate packing 457 in close contact with the first tapered inner circumferential surface 435*t*1 of the stepped portion 435*b* of the central section 435 (the second-packing-pressing step).

Next, the wire packing 459, which is to become the first packing 459, is inserted into the metallic shell 431, and is disposed in the clearance (clearance 420) between the second tapered outer circumferential surface 421*t*2 of the element holder 421 and the inner circumferential surface 431*n* of the metallic shell 431 (the wire-packing-inserting step).

Next, the wire packing 459 is axially pressed toward the distal end of the gas sensor 401 so as to be plastically deformed in the axial direction, thereby forming the first packing 459 in the same manner as in the above-described embodiments (the first-packing-forming step). Thus, the wire packing 459 is plastically deformed such that its cross-sectional shape changes from a circular shape to a wedge shape, and is strongly pressed against the second tapered outer circumferential surface 421*t*2 of the element holder 421 and the central inner circumferential surface 435*n* of the central section 435 of the metallic shell 431.

Next, in order to form the charged seal layer 461, a powder that contains talc as a main component is charged into a clearance provided between the outer circumferential surface 411*m* of the gas detection element 411 and the inner circumferential surface 431*n* of the metallic shell 431.

Subsequently, the insulator 471 is inserted into the above clearance, and is axially pressed. Then, the wire packing 465 is inserted, and the tip end of the proximal end section 437 of the metallic shell 431 is bent radially inward, thereby performing compressive crimping in the axial direction. Further, the protection cap 451 is attached to the distal end of the metallic shell 431, and the gasket 453 is attached to the metallic shell 431.

Meanwhile, the sensor output leads 483 and 484 are connected to the sensor terminal metal pieces 487 and 488, and the heater lead wires 485 and 486 are connected to the heater terminal metal pieces 491 and 492. These are attached to the separator 481, and the proximal end portion 412 of the gas detection element 411 is also inserted into the separator 481. After that, the separator 481 and the grommet 477 are inserted into the metal sleeve 475 and are fixed thereto. Subsequently, the metal sleeve 475 and the metallic shell 431 are fixed together by means of laser welding.

Thus, the gas sensor 401 is completed.

As described above, according to the method of manufacturing the gas sensor 401 of the present embodiment, in the second-packing-pressing step, the plate packing (the second packing) 457 is axially pressed to thereby be brought into close contact with the first tapered inner circumferential surface (the support surface) 435*t*1 of the stepped portion 435*b* of the metallic shell 431. Therefore, good contact is established between the plate packing 457 and the metallic shell 431.

In the first-packing-forming step, the wire packing 459 is axially pressed, to thereby be plastically deformed such that the wire packing (the first packing) 459 is strongly pressed against the second tapered outer circumferential surface 421*t*2 of the element holder 421 and the central inner circumferential surface 435*n* of the central section 435 of the metallic shell 431. Thus, even when no external stress is exerted on the first packing 459, the first packing 459 can fix the element holder (to-be-held member) 421 in the metallic shell 431. Therefore, even when, as a result of long-term use of the gas sensor 401, loosening of the crimp or a like phenomenon occurs, the first packing 459 is less likely to become loose as compared with a conventional counterpart, and positional shift of the element holder 421 is suppressed. Additionally, since the above-described first packing 459 is formed by plastically deforming a wire packing 459, the gas sensor 401 can be easily manufactured at low cost.

While the present invention has been described with reference to embodiments, the present invention is not limited thereto. The present invention may be embodied in various other forms without departing from the scope of the invention.

For example, the above embodiments use wire packings (C type) as the wire packings 159, 165, etc. However, an annular wire packing may be used. The annular wire packing can reliably enhance sealing performance.

The first embodiment uses the annular plate packing 157, etc. as the second packing. However, a wire packing (C type) may be used as the second packing.

In the first embodiment, the gas detection element 111 and the metallic shell 131 are electrically connected by means of the plate packing 157. However, the present invention is not limited thereto. When the first packing 159 is made of metal, the gas detection element 111 and the metallic shell 131 can also be electrically connected by means of the first packing 159. Notably, since the first packing 159 is pressed against the second tapered outer circumferential surface 113t2 of the projection 113 and the inner circumferential surface 131n of the metallic shell 131 in a surface-to-surface contact relation, the first packing 159 can reliably establish electrical connection between the gas detection element 111 and the metallic shell 113.

The invention claimed is:

1. A gas sensor comprising:
a to-be-held member including a distal-end-side holding surface and a proximal-end-side holding surface located on the proximal end side with respect to the distal-end-side holding surface;
a tubular metallic shell including a stepped portion projecting radially inward from its inner circumferential surface, and adapted to hold the to-be-held member therein while surrounding the to-be-held member from radially outside and supporting the distal-end-side holding surface of the to-be-held member by a support surface of the stepped portion; and
a first metallic packing abutting the proximal-end-side holding surface of the to-be-held member and the inner circumferential surface of the metallic shell, wherein
the first packing is disposed in an acute-angle clearance formed between the proximal-end-side holding surface of the to-be-held member and the inner circumferential surface of the metallic shell such that the first packing has a wedge-like cross section and is pressed against the proximal-end-side holding surface of the to-be-held member and the inner circumferential surface of the metallic shell, and
the first packing is formed by axially pressing and plastically deforming a wire packing, which has been inserted into the clearance between the proximal-end-side holding surface of the to-be-held member and the inner circumferential surface of the metallic shell, such that the first packing has a wedge-like cross-section.

2. A gas sensor according to claim 1, wherein the to-be-held member is a gas detection element having a projection which includes the distal-end-side holding surface and the proximal-end-side holding surface and which projects radially outward, the gas detection element assuming a closed-bottomed tubular shape with an axially distal end closed.

3. A gas sensor according to claim 1, further comprising a gas detection element extending along the axial direction, wherein the to-be-held member is an element holder which has the distal-end-side holding surface, the proximal-end-side holding surface, and an opening through which the gas detection element is passed.

4. A gas sensor according to claim 2, further comprising a charged seal layer, which is formed by means of charging a powder into a clearance between the outer circumferential surface of the gas detection element and the inner circumferential surface of the metallic shell in a region located toward the proximal end of the gas sensor with respect to the first packing.

5. A gas sensor according to claim 3, further comprising a charged seal layer, which is formed by means of charging a powder into a clearance between the outer circumferential surface of the gas detection element and the inner circumferential surface of the metallic shell in a region located toward the proximal end of the gas sensor with respect to the first packing.

6. A gas sensor according to claim 1, wherein the first packing is formed by axially pressing and plastically deforming a wire packing, which has been inserted into the clearance between the proximal-end-side holding surface of the to-be-held member and the inner circumferential surface of the metallic shell, such that the first packing has a wedge-like cross section.

7. A gas sensor according to claim 1, wherein
the proximal-end-side holding surface of the to-be-held member and the inner circumferential surface of the metallic shell assume respective shapes such that in at least a distal-end-side portion of the clearance, the angle formed by the proximal-end-side holding surface and the inner circumferential surface decreases toward the distal end side; and
the first packing is disposed to extend to the portion of the clearance where the angle formed by the proximal-end-side holding surface and the inner circumferential surface decreases toward the distal end side.

8. A gas sensor comprising:
a gas detection element assuming a closed-bottomed tubular shape with an axially distal end closed, including an outer electrode formed on its outer circumferential surface, and including a projection projecting radially outward;
a tubular metallic shell including a stepped portion projecting radially inward from its inner circumferential surface, and adapted to hold the gas detection element therein while surrounding the gas detection element from radially outside and supporting a distal end surface of the projection by a support surface of the stepped portion, the support surface of the stepped portion abutting the outer electrode formed on the distal end surface of the projection to thereby be electrically connected with the outer electrode; and
a first metallic packing abutting a proximal end surface of the projection and the inner circumferential surface of the metallic shell, wherein
the first packing is disposed in an acute-angle clearance formed between the proximal end surface of the projection and the inner circumferential surface of the metallic shell such that the first packing has a wedge-like cross section and is pressed against the proximal end surface of the projection and the inner circumferential surface of the metallic shell, and
the first packing is formed by axially pressing and plastically deforming a wire packing, which has been inserted into the clearance between the proximal end surface of the projection and the inner circumferential surface of the metallic shell, such that the first packing has a wedge-like cross section.

9. A gas sensor according to claim 8, further comprising a charged seal layer, which is formed by means of charging a powder into a clearance between the outer circumferential surface of the gas detection element and the inner circumferential surface of the metallic shell in a region located toward the proximal end of the gas sensor with respect to the projection of the gas detection element.

10. A gas sensor according to claim 8, the first packing abuts the outer electrode formed on the proximal end surface of the projection and the inner circumferential surface of the metallic shell to thereby electrically connect the outer electrode and the metallic shell.

11. A gas sensor according to claim 8, wherein the proximal end surface of the projection and the inner circumferential surface of the metallic shell assume respective shapes such that in at least a distal-end-side portion of the clearance, the angle formed by the proximal end surface and the inner circumferential surface decreases toward the distal end side; and the first packing is disposed to extend to the portion of the clearance where the angle formed by the proximal end surface and the inner circumferential surface decreases toward the distal end side.

12. A gas sensor comprising:

a gas detection element assuming a closed-bottomed tubular shape with an axially distal end closed, including an outer electrode formed on its outer circumferential surface, and having a projection projecting radially outward;

a tubular metallic shell including a stepped portion projecting radially inward from its inner circumferential surface, and adapted to hold the gas detection element therein while surrounding the gas detection element from radially outside and supporting a distal end surface of the projection by a support surface of the stepped portion;

a first metallic packing abutting a proximal end surface of the projection and the inner circumferential surface of the metallic shell; and a second packing of metal disposed between the distal end surface of the projection and the support surface of the stepped portion, and abutting the support surface of the stepped portion and the outer electrode formed on the distal end surface of the projection to thereby electrically connect the metallic shell and the outer electrode, wherein the first packing is disposed in an acute-angle clearance formed between the proximal end surface of the projection and the inner circumferential surface of the metallic shell such that the first packing has a wedge-like cross section and is pressed against the proximal end surface of the projection and the inner circumferential surface of the metallic shell, and the first packing is formed by axially pressing and plastically deforming a wire packing, which has been inserted into the clearance between the proximal end surface of the projection and the inner circumferential surface of the metallic shell, such that the first packing has a wedge-like cross section.

13. A gas sensor according to claim 12, further comprising a charged seal layer, which is formed by means of charging a powder into a clearance between the outer circumferential surface of the gas detection element and the inner circumferential surface of the metallic shell in a region located toward the proximal end of the gas sensor with respect to the projection of the gas detection element.

14. A gas sensor according to claim 12, the first packing is abuts the outer electrode formed on the proximal end surface of the projection and the inner circumferential surface of the metallic shell to thereby electrically connect the outer electrode and the metallic shell.

15. A gas sensor according to claim 12, wherein the proximal end surface of the projection and the inner circumferential surface of the metallic shell assume respective shapes such that in at least a distal-end-side portion of the clearance, the angle formed by the proximal end surface and the inner circumferential surface decreases toward the distal end side; and the first packing is disposed to extend to the portion of the clearance where the angle formed by the proximal end surface and the inner circumferential surface decreases toward the distal end side.

16. A method of manufacturing a gas sensor comprising:

a gas detection element assuming a closed-bottomed tubular shape with an axially distal end closed, including an outer electrode formed on its outer circumferential surface, and including a projection projecting radially outward;

a tubular metallic shell including a stepped portion projecting radially inward from its inner circumferential surface, and adapted to hold the gas detection element therein while surrounding the gas detection element from radially outside and supporting a distal end surface of the projection by a support surface of the stepped portion, the support surface of the stepped portion abutting the outer electrode formed on the distal end surface of the projection to thereby be electrically connected with the outer electrode; and a first metallic packing abutting a proximal end surface of the projection and the inner circumferential surface of the metallic shell, the method comprising:

an element-inserting step of inserting the gas detection element into the metallic shell;

a wire-packing-inserting step of inserting a wire packing, which is to become the first packing, into the metallic shell; and a first-packing-forming step of axially pressing the wire packing inserted into the metallic shell such that the wire packing is plastically deformed so as to form the first packing which is disposed in an acute-angle clearance formed between the proximal end surface of the projection and the inner circumferential surface of the metallic shell such that the first packing has a wedge-like cross section and is pressed against the proximal end surface of the projection and the inner circumferential surface of the metallic shell.

17. A method of manufacturing a gas sensor, said gas sensor comprising:

a gas detection element assuming a closed-bottomed tubular shape with an axially distal end closed, having an outer electrode formed on its outer circumferential surface, and including a projection projecting radially outward;

a tubular metallic shell including a stepped portion projecting radially inward from its inner circumferential surface, and adapted to hold the gas detection element therein while surrounding the gas detection element from radially outside and supporting a distal end surface of the projection by a support surface of the stepped portion;

a first metallic packing abutting a proximal end surface of the projection and the inner circumferential surface of the metallic shell; and a second packing of metal disposed between the distal end surface of the projection and the support surface of the stepped portion, and abutting the outer electrode formed on the distal end surface of the projection and the support surface of the stepped portion to thereby electrically connect the outer electrode and the metallic shell, said method comprising:
a second-packing-inserting step of inserting the second packing into the metallic shell;
an element-inserting step of, after the second-packing-inserting step, inserting the gas detection element into the metallic shell;
a second-packing-pressing step of, after the element-inserting step, axially pressing the gas detection element and the second packing inserted into the metallic shell to thereby bring the second packing into close contact with the support surface of the stepped portion;
a wire-packing-inserting step of, after the second-packing-pressing step, inserting a wire packing, which is to become the first packing, into the metallic shell; and
a first-packing-forming step of axially pressing the wire packing inserted into the metallic shell such that the wire packing is plastically deformed so as to form the first packing which is disposed in an acute-angle clearance formed between the proximal end surface of the projection and the inner circumferential surface of the metallic shell such that the first packing has a wedge-like cross section and is pressed against the proximal end surface of the projection and the inner circumferential surface of the metallic shell.

* * * * *